US009546902B2

United States Patent
Kovacich et al.

(10) Patent No.: US 9,546,902 B2
(45) Date of Patent: Jan. 17, 2017

(54) METHOD AND SYSTEM FOR CORRECTING INCIDENT LIGHT FLUCTUATIONS IN ABSORPTION SPECTROSCOPY

(71) Applicant: Servomex Group Limited, Crowborough, East Sussex (GB)

(72) Inventors: Richard P. Kovacich, Crowborough (GB); Bahram Alizadeh, Kent (GB); Ian C. Gaskin, Kent (GB); James D. Hobby, Crowborough (GB); Martin Lopez, Rotherfield (GB)

(73) Assignee: Servomex Group Limited (GB)

( * ) Notice: Subject to any disclaimer, the term of this patent is extended or adjusted under 35 U.S.C. 154(b) by 0 days.

(21) Appl. No.: 14/662,307

(22) Filed: Mar. 19, 2015

(65) Prior Publication Data
US 2015/0268095 A1 Sep. 24, 2015

(30) Foreign Application Priority Data

Mar. 24, 2014 (GB) .................................. 1405247.6

(51) Int. Cl.
*G01N 21/00* (2006.01)
*G01J 3/02* (2006.01)
(Continued)

(52) U.S. Cl.
CPC .............. *G01J 3/027* (2013.01); *G01J 3/0297* (2013.01); *G01J 3/10* (2013.01); *G01J 3/433* (2013.01);
(Continued)

(58) Field of Classification Search
CPC ...... G01N 21/274; G01N 21/39; G01N 21/59; G01J 3/027; G01J 3/42; G01J 3/433
(Continued)

(56) References Cited

U.S. PATENT DOCUMENTS 3,856,406 A 12/1974 Noble et al.
6,040,914 A 3/2000 Bortz et al.
(Continued)

FOREIGN PATENT DOCUMENTS

DE 10 2011 080 086 A1 1/2013
EP 1 510 798 B1 8/2003
(Continued)

OTHER PUBLICATIONS

Search and Examination Report dated May 7, 2014 for Great Britain Application No. 1405247.6; 7 pages.
(Continued)

*Primary Examiner* — Hoa Pham
(74) *Attorney, Agent, or Firm* — Daly, Crowley, Mofford & Durkee, LLP

(57) ABSTRACT

A method and system for correcting the effect of intensity fluctuations of the transmitted light in an absorption spectroscopy system used for the detection or measurement of chemical species in a medium, whereby one or more modulation bursts are imposed onto a light beam that passes through the medium. This burst signal may be obtained by modulating the bias current of a tunable diode laser, and the modulation burst signal may be optimally at the second harmonic of the modulation frequency of a wavelength modulated beam to allow usage of the same signal path processing used for the spectroscopic detection of the measurand for a second harmonic detection system. The burst signal can be controlled using a smooth window function to minimise the effects of non-linear perturbations that are inherent in tunable diode laser wavelength modulation spectroscopy systems, of optical interference fringes (etalons) and of the residual light absorption by background chemical species or the measurand at the wavelength coinciding with the modulation burst.

39 Claims, 11 Drawing Sheets

(51) Int. Cl.
*G01J 3/10* (2006.01)
*G01J 3/433* (2006.01)
*G01N 21/39* (2006.01)
*G01N 21/27* (2006.01)
*G01J 3/42* (2006.01)

(52) U.S. Cl.
CPC ............ *G01N 21/274* (2013.01); *G01N 21/39* (2013.01); *G01J 2003/423* (2013.01); *G01N 2021/399* (2013.01); *G01N 2201/0612* (2013.01); *G01N 2201/121* (2013.01); *G01N 2201/1215* (2013.01)

(58) Field of Classification Search
USPC ................. 356/437, 326, 318, 243.1, 451
See application file for complete search history.

(56) References Cited

U.S. PATENT DOCUMENTS

| | | | | |
|---|---|---|---|---|
| 6,611,335 | B1* | 8/2003 | Hovde | G01N 21/39 356/437 |
| 6,657,198 | B1 | 12/2003 | May | |
| 6,940,599 | B1 | 9/2005 | Hovde | |
| 7,116,422 | B2* | 10/2006 | Larking | G01J 3/433 356/437 |
| 9,261,453 | B2* | 2/2016 | Steinbacher | G01N 21/39 |
| 2005/0140979 | A1* | 6/2005 | Kluczynski | G01J 3/4338 356/425 |
| 2006/0044562 | A1 | 3/2006 | Hagene et al. | |
| 2009/0201507 | A1* | 8/2009 | Kluczynski | G01J 3/4338 356/437 |
| 2010/0292581 | A1* | 11/2010 | Howard | G01J 3/0205 600/476 |
| 2014/0247843 | A1* | 9/2014 | Steinbacher | H01S 5/06808 372/20 |
| 2016/0047739 | A1* | 2/2016 | Bitter | G01N 21/31 356/402 |

FOREIGN PATENT DOCUMENTS

| | | |
|---|---|---|
| EP | 1 510 798 A1 | 3/2005 |
| EP | 2 072 979 A1 | 6/2009 |
| EP | 2 072 979 B1 | 2/2012 |
| WO | WO 2011/160013 | 12/2011 |
| WO | WO 2013/127657 A1 | 9/2013 |

OTHER PUBLICATIONS

Response to Search and Examination Report filed in the UK IPO on Nov. 3, 2014 for Great Britain Application No. 1405247.6; 22 pages.
Indication of Allowability dated Nov. 13, 2014 for Great Britain Application No. 1405247.6; 1 page.
Atmospheric $CH_4$ and $H_2O$ Monitoring With Near-Infrared InGaAs Laser Diodes by the SDLA, a Ballonborne Spectrometer for Tropospheric and Stratospheric in Situ Measurements; Georges Durry and Gerard Megie; Applied Optics, vol. 36,No. 36, pp. 7342-7354 (1999).
Comparison of a quantum cascade laser used in both cw and pulsed modes. Application to the study of $SO_2$ lines around 9 µm, B. Grouiez, B. Parvitte, L. Joly, D. Courtois, V. Zeninari; Applied Physics B, vol. 90, pp. 177-186 (2008).
Measurements of $CO_2$ concentration and temperature at high pressures using 1$f$-normalized wavelength modulation spectroscopy with second harmonic detection near 2.7 µm; A. Farooq, J.B Jeffries, and R.K Hanson; Applied Optics, vol. 48, No. 35, pp. 6740-6753 (2009).
Recovery of Absolute Gas Absorption Line Shapes Using Tunable Diode Laser Spectroscopy With Wavelength Modulation—Part I: Theoretical Analysis; George Stewart, Walter Johnstone, James R.P Bain, Keith Ruxton, and Kevin Duffin; Journal of Lightwave Technology, vol. 29, No. 6, pp. 811-821 (2011).
Saturation of silicon photodiodes at high modulation frequency; M. Young and R. A. Lawton; Applied Optics, vol. 17,No. 7, pp. 1103-1106 (1978).
Partial European Search Report dated Oct. 28, 2015 corresponding to European Application No. 15159658.2; 7 Pages.
Extended European Search Report and Opinion dated Apr. 12, 2016 corresponding to European Application No. 15159658.2; 12 Pages.
Response to European Search Opinion (w/amended claims) dated Apr. 12, 2016 corresponding to European Application No. 15159658.2; Response filed Oct. 27, 2016; 17 Pages.
Great Britain Intention to File Divisional Application dated Feb. 2, 2016 corresponding to Great Britain Application No. GB1405247.6; 2 Pages.
Great Britain Notification of Grant dated Mar. 1, 2016 corresponding to Great Britain Application No. GB1405247.6; 2 Pages.

* cited by examiner

METHOD AND SYSTEM FOR CORRECTING INCIDENT LIGHT FLUCTUATIONS IN ABSORPTION SPECTROSCOPY

CROSS REFERENCE TO RELATED APPLICATIONS

This application claims priority under 35 U.S.C. §119 to United Kingdom patent application No, GB 1405247.6 filed on Mar. 24, 2014, which is incorporated herein by reference in its entirety.

FIELD OF THE INVENTION

This invention relates to absorption spectroscopy in general and to tunable diode laser absorption spectroscopy in particular. The invention has applications in, among other things, the detection and measurement of one or more species in a gas produced by an artificial or natural process such as an industrial, medical or physiological process.

BACKGROUND

Tunable laser wavelength modulation spectroscopy is finding widespread use in various applications. One such application is the quantification of the amount of chemical species (the measurand) in a substance and in particular in an artificial or natural process such as an industrial, medical or physiological process gas analysis where traditional techniques are either unsuitable or poor.

A typical system consists of a tunable laser source such as a tunable diode laser (TDL) that emits a beam of light that is focussed on a detector. The substance that is to be analysed is positioned between the tunable laser source and the detector, so that the light incident on the detector has been modified by its passage through the substance. The modifications to the light enable various parameters of the measurand to be determined by a signal processing system that is coupled to the detector. In some cases the substance to be analysed is a gas produced by an industrial process, and the measurand may be one or more chemical species that are present in this process gas. Examples of measurand species include but are not limited to gaseous water, $O_2$, CO and $CO_2$ and hydrocarbons such as methane. The presence and/or amount fraction (concentration) of one or more of these measurand species may be determined using one or more TDLs.

In operation of the laser gas analyser system, the wavelength of the beam emitted by the TDL is scanned over one or more absorption lines of the measurand. At certain specific wavelengths within the range of wavelengths scanned, light is absorbed by the measurand and these spectral absorption lines can be detected by measuring the light transmitted through the substance to be analysed. This allows the necessary spectroscopic information to be acquired to determine not only the amount fraction of the measurand, but also the influence of pressure, temperature or background mixture composition. In some cases it is possible to use a single laser source to measure a plurality of measurands. In these cases, the output wavelength of the laser source is swept across a wavelength range that includes at least one discernable absorption line for each of the plurality of measurands.

In a well-designed system, wavelength modulation techniques offer very high sensitivity and enhanced spectral resolution. In particular, second harmonic wavelength modulation spectroscopy is well suited to gas analysis due to its ability to cope with a wide variety of spectroscopic situations found in industrial processes that includes congested absorption spectra, sensitive trace level measurements and obscured optical transmission.

The detector response is proportional to the intensity of light transmitted through the substance under test, which is dependent on the intensity of light transmitted through the substance under test as well as the amount fraction of measurand at the absorbing wavelengths. Therefore fluctuations of the light intensity caused by either the laser source or transmission through the analysed substance will cause uncertainty in the measurement of the amount fraction of measurand.

This is shown by the following relationships, where equation [1] represents the Beer-Lambert law of optical absorption, wherein u is the molecular density per unit length of the measurand, I is the detected amount of light, $I_0$ is the incident amount of light (equal to unabsorbed amount when the molecular density is zero), v is the frequency of light and k is the absorption coefficient.

$$\log\left[\frac{I(v)}{I_0(v)}\right] = -uk(v) \quad [1]$$

The change in the amount of light detected at any particular frequency ($\partial I(v)$) is related to the molecular density change ($\partial u$) as given by equation [2], which also shows the uncertainty term due to variation of the incident amount of light ($\partial I_0$)

$$\partial u = \frac{\frac{\partial I_0(v)}{I_0(v)} - \frac{\partial I(v)}{I(v)}}{k(v)} \quad [2]$$

Variations in incident light intensity at the detector may be caused by a number of factors other than the concentration of the measurand. For example, variations can be caused by intrinsic fluctuations in the laser output, changes in ambient light intensity levels and/or obscuration in the process sample stream, which may be caused by any combination of dust, tar, corrosion or optical beam misalignment. Obscuration and changing of the intensity of ambient light are to be expected in a furnace. If the variation in incident light is not corrected, this will result in a measurement uncertainty in the processed measurand concentration. Some prior art techniques have been developed to deal with these sources of error. However, the techniques are not well suited for use with TDLs.

One known technique to reduce errors from ambient light is to use interference filters to block a large amount of the broadband light from an ambient light source. However, it is unavoidable that a small but significant amount of ambient light will get through the filter pass band used for the measurement. A prior art technique for negating the error introduced by this residual ambient light is to periodically turn off the laser. This allows the level of residual ambient light to be measured and corrected for. Specifically, the difference in detector signal between the on and off states indicates the amount of incident laser light, thus allowing the residual ambient light to be determined and compensated for. To make use of this technique, however, the laser must be turned off frequently, since ambient light levels will typically vary unpredictably over relatively short timescales, and this technique is not well suited for use with a tunable diode laser. The problem is that repeatedly turning the diode laser on and off causes significant ohmic heating within the diode laser, which is problematic because ohmic heating also affects the wavelength of the output beam of the laser. This dynamic response is referred to as ohmic heating perturbation. Consequently, when this technique is used with TDLs, the laser wavelength scan suffers from large linearity errors, which distorts the measured absorption line shape.

One possible technique to address the error caused by intrinsic fluctuations in the laser output power is to monitor the laser output power while measurements are being made. The laser output power can be monitored at a 'neutral' wavelength that is not absorbed by the measurand or other interfering chemical species, and this signal can be compared with a reference value to allow any variations to be corrected for. This results in the measured signal being standardised to a reference value for the amount of incident light. This technique may not be practical in a congested absorption spectrum and could lead to errors.

An alternative method of compensating for variations in the incident light caused by fluctuations in the laser output power is to simultaneously perform second harmonic wavelength modulation spectroscopy and first harmonic modulation spectroscopy. First and second harmonic modulation spectroscopy is known to those skilled in the art and will not be described further here. By taking the ratio of the second harmonic signal to the first harmonic signal, a quantity is obtained that is theoretically independent of the incident light variation for the optically thin regime i.e. weak absorption. However, the inclusion of the first harmonic signal negates the enhanced spectral resolution advantage of using the second harmonic signal alone. Therefore, any interfering background absorption will cause measurement uncertainty of the ratio. This means that this technique is not well suited to situations where many different species are present alongside the measurand, particularly if these species have absorption lines close to or even overlapping those of the measurand. This is often the case in a process gas that is output from an industrial process, for example. In addition, the implementation is more difficult than a standard wavelength modulation spectroscopy system as two separate signal processing channels are required for simultaneous first and second harmonic detection.

A further complication with this technique when used with TDLs is that the residual amplitude modulation (RAM), which is always present when modulating laser diodes using the bias current, adds additional measurement uncertainty to the above ratio. Although the RAM uncertainty can be corrected for by characterising the diode laser intensity modulation behaviour, these modulation characteristics change with the diode laser temperature and bias current settings. The diode laser is normally temperature controlled, which is necessary to achieve frequency stability, and, in an ideal situation, the diode laser temperature is unconditionally stable and hence the modulation characteristics are also stable. However, for a rugged industrial analyser that must cope with wide ambient temperature swings, even the best diode laser temperature control will experience some residual temperature change due to finite thermal control gain. In some cases, the residual temperature change may be significant enough to require retuning of the diode laser frequency onto the measurement absorption line.

Furthermore, the amount of RAM is dependent on the frequency modulation sensitivity of the diode laser as the bias current modulation amplitude is adjusted to achieve sufficient frequency modulation range in order to obtain adequate signal from the wavelength modulation spectroscopy. However, the frequency modulation sensitivity varies among different types of diode lasers. For example, distributed feedback (DFB) structure laser diodes have comparatively low frequency modulation sensitivity, typically less than 0.1 $cm^{-1}$ per milliamp bias current resulting in large RAM, whereas, vertical cavity semiconductor emitting lasers (VCSEL) tend to have much larger frequency modulation sensitivity, typically greater than 5 $cm^{-1}$ per milliamp bias current resulting in much lower RAM. There remains a need for an absorption spectroscopy gas analyser system that can produce highly accurate measurements despite fluctuations in the intensity of the transmitted light. There is also a need for such an analyser system that is able to produce highly accurate measurements in a harsh environment as may typically be found in many industrial processes, such as in a furnace or furnace exhaust pipe.

SUMMARY

In a first aspect of the invention, there is provided a method of correcting for the effects of intensity fluctuations of incident light within an absorption spectroscopy system, comprising the steps of:

controlling a light source to emit a wavelength modulated beam of light;

applying at least one modulation burst signal to modulate the wavelength modulated beam and/or to modulate a separate beam synchronised with the wavelength modulated beam, which at least one modulation burst signal is a tapering signal modulation;

detecting the modulated beam or beams of light after transmission through a test medium;

processing the detected beam or beams to obtain at least one detected burst signal and to measure absorption effects of one or more measurands, wherein the processing includes comparing the at least one detected burst signal with the applied at least one modulation burst signal to determine intensity fluctuations of the incident light that are separate from absorption effects of the measurand(s), and correcting for the effects of the determined intensity fluctuations for increased accuracy of measurement of the absorption effects of the measurand(s).

In an embodiment, a wavelength zone is selected for a desired burst signal location and duration. This may involve selecting one or more wavelength zones that are separate from absorption lines of the measurand(s), and possibly separated from absorption lines of any constituents of the test medium. This can be based on known spectroscopic absorption data or a calibration process may be used to select the optimum burst signal locations, to identify a "neutral" wavelength zone.

The method is well suited to measurement of the amount fraction of one or more measurand species in a gas containing volume, for an artificial or natural process, such as for medical, physiological or industrial process gas analysis. This measurement could be in situ such as across a furnace or the exhaust pipe of a furnace or other industrial process chamber or gas cell, or it could take place in an extractive system, for example including gas conditioning means such as involving temperature control and/or dehumidification. The measurement could involve a single light beam pass measurement or a multi-pass measurement using a retro reflector or other suitable means such as a White or Heriott cell arrangement to extend the effective light path within a confined length. Such arrangements for extending the light path are known to those skilled in the art and will not be discussed further here.

The method of correcting is particularly suited to tunable diode laser absorption spectroscopy, where the diode laser can be controlled by applying a modulated control signal to the diode laser's bias current. In an embodiment, the application of the burst signal involves applying a modulation burst signal to the modulated control signal of the laser light source. In an embodiment, the burst signal is controlled using a smooth window function or envelope function that achieves a tapering signal modulation without sharp signal transitions. The window function can be used to control the rate of change of a tunable diode laser's bias current and the sharpness of signal transitions, either via amplitude modulation at fixed phase, or phase modulation at fixed amplitude, or a combination of amplitude and phase modulation. This is advantageous because sudden signal transitions such as caused by interrupting the diode laser bias current can cause significant ohmic heating perturbation, which changes the wavelength of light emitted by a tunable diode laser, as well as causing "ringing" (oscillating amplitude variations that take time to settle) or ripple (phase variations) at a demodulation filter of the detection electronics. Such problems reduce the accuracy of the calculation of intensity fluctuations. The inventors of the present invention have determined that application of a smoothly tapering burst modulation signal can avoid unwanted wavelength changes and signal processing errors, such that an improved error correction can be achieved via measurement of the applied burst signal.

In an embodiment, a tunable diode laser's bias current is repeatedly ramped up and down to generate a wavelength modulated laser beam that repeatedly scans across a range of wavelengths, at a scan rate having a period T, and a burst signal modulation is applied to the bias current. The duration of the burst signal is less than the period T. Although the bias current to the diode laser is ramped up and down, the bias current is preferably maintained as a continuous current rather than being periodically interrupted and switched back on, to avoid the ohmic heating perturbation effects that would be caused by repeatedly switching the laser on and off. If a plurality of burst signals are applied, the total duration of the plurality of burst signals is preferably less than T. The burst signal may occur within the same scan as the measurand absorption feature or within a separate scan, not including the measurand absorption feature, but close in time compared to the measurand scan.

In an embodiment, information is encoded in the output beam of a diode laser by applying a modulation to the bias current of the laser diode, which produces a corresponding modulated burst signal in the output beam of the laser diode. This burst signal is detectable by an optical detection means and subsequent processing can be applied to the signal produced by the optical detection means to extract the information encoded in the laser beam. Comparing the extracted information with the known input information fives an indication of the effects of background radiation (e.g. light emitted by substances heated in a furnace) and obscuration (light which is not transmitted due to dust for example). By measuring fluctuations in the intensity of the laser's output beam and correcting for them, the amount fraction of a measurand can be measured more accurately. It is possible to use the information encoded in the beam to correct for fluctuations in the ambient light level without having to switch the laser off in order to directly measure the ambient light level.

Some embodiments of the invention apply a burst signal having an optimal amplitude modulation and/or phase modulation, which can be determined by calibration, to mitigate problems of ohmic heating within the laser light source and to avoid exciting an impulse response within processing electronics associated with a photodetector. The processing is applied to a signal output by the photodetector. The processing of the detected beam preferably comprises demodulating a signal output by the photodetector, to obtain a reference signal representing incident light produced by the burst signal, and using the reference signal to correct the measurement of a measurand for fluctuations in the light incident on the photodetector. The modulation burst signal enables background effects to be determined without interruption of the laser's bias current. The location and duration of the burst signal can be selected for easy differentiation between the but signal and the measured absorption lines of the measurand.

In an embodiment, the burst signal comprises a modulation burst signal applied to a tunable diode laser modulation signal at the second harmonic of the modulation frequency, to enable detection using detection electronics operating at the second harmonic of the high frequency modulation of the wavelength modulated tunable diode laser. The advantages of using this technique include quicker and more efficient signal processing and also any inherent instrumentation effects are minimised or "nulled out" by using a common signal processing path for both the measurand and burst signals.

Another aspect of the invention provides an absorption spectroscopy system, comprising:
  a light source for emitting a photon beam;
  a controller for controlling the light source to emit a wavelength modulated beam of light, wherein the controller is adapted to apply at least one tapering burst signal modulation to the emitted beam;
  a photodetector for detecting the modulated beam of light after transmission through a test medium;
  a signal processing unit for processing the detected beam to obtain at least one detected burst signal and to measure absorption effects of one or more measurands, wherein the processing unit is adapted to compare the at least one detected burst signal with the applied at least one burst signal to determine intensity fluctuations of the incident light that are separate from absorption effects of the measurand(s), and to correct for the effects of the determined intensity fluctuations for increased accuracy of measurement of the absorption effects of the measurand(s).

In an embodiment, the controller is adapted to generate a modulated control signal including a tapering burst signal modulation, such as modulating the bias current of a tunable diode laser light source.

BRIEF DESCRIPTION OF THE DRAWINGS

Preferred embodiments of the present invention are described below, by way of example only, with reference to the following drawings in which.

DETAILED DESCRIPTION OF EMBODIMENTS

Figure 1:
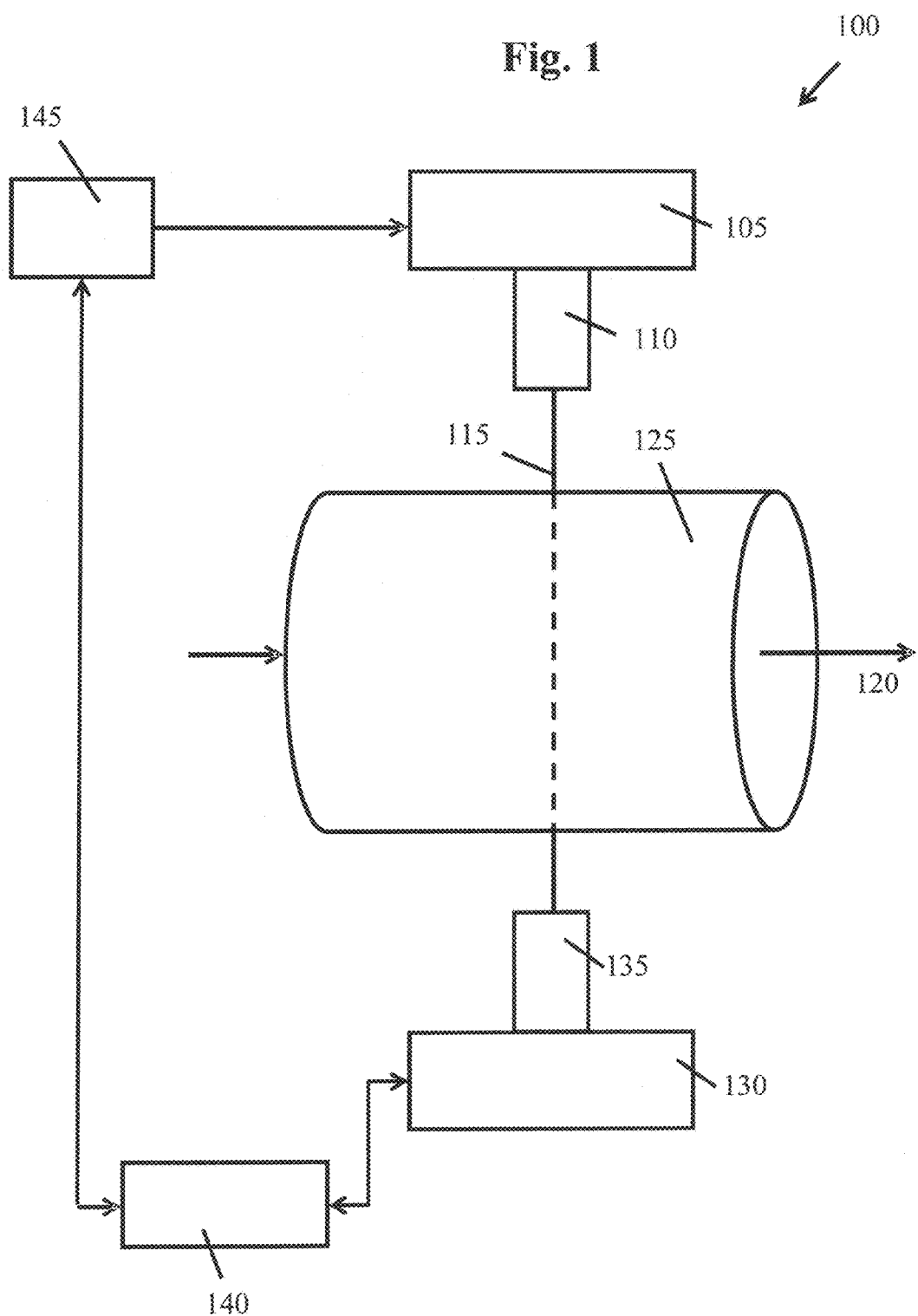
FIG. 1 is a schematic diagram of a laser gas analyser system deployed as an industrial process gas analyser.

Embodiments of the invention are best understood in the context of the broader system in which they operate. FIG. 1 shows, in schematic form, the major components of a typical laser gas analyser system 100. System 100 includes a laser 105, which may be a tunable laser such as a tunable diode laser (TDL). Tunable diode lasers are well known to the skilled person and so will not be described in further detail here.

Optionally, a laser mount 110 may be provided to secure laser 105 in position. If present, preferably laser mount 110 allows fine adjustment to the angle of laser 105 to facilitate beam alignment. Laser mount 110 may include a window (not shown) that is transparent to at least the wavelengths of light emitted by laser 105.

Laser 105 emits a beam 115 of a specific wavelength $\lambda$. Where laser 105 is a tunable laser, $\lambda$ can be varied by a controller 145 of the laser 105 using methods known to those skilled in the art. For example, in the case of a TDL, $\lambda$ can be varied by adjusting one or both of the temperature of the laser and the diode bias current. Typically the bias current is varied so as to cause $\lambda$ to vary as a function of time in a manner that causes it to sweep across one or more absorption lines corresponding to the measurand species that the system is to detect and in some preferred embodiments, the bias current to the diode laser may be continuous and variable to avoid the effects of ohmic heating perturbation (that could arise if the diode laser was periodically interrupted and switched back on in order to measure ambient light levels). Sweep frequencies of the order of several hundred hertz may be achieved. $\lambda$ may be in the near-infrared portion of the electromagnetic spectrum. $\lambda$ may be in the range of about 200 nm to about 10000 nm. $\lambda$ will be chosen by the skilled person depending on the measurand species and the need for the wavelength range of the TDL to encompass one or more absorption peaks of the measurand species.

Beam 115 is directed such that it passes through a volume containing a sample that is to be analysed. In the embodiment of FIG. 1, the sample is a gas mixture 120 that is produced in or flowing through a chamber 125, but it will be appreciated that variations to this arrangement will be made according to the environment that system 100 is deployed in. Chamber 125 may be a furnace or a pipe such as a furnace exhaust pipe or a gas cell. Gas mixture 120 may be the gases produced by an industrial process, such as furnace exhaust gases, or gases used in artificial or natural process applications. A window (not shown) may be provided in chamber 125, to allow beam 115 to penetrate chamber 125 and pass through gas mixture 120. Mother window not shown) may be provided in chamber 125 to allow beam 115 to exit chamber 125.

System 100 also includes a detector 130 that is capable of detecting light at the wavelengths emitted by laser 105. Detector 130 may be a photodetector of any type known to the skilled person, e.g. a photo diode. Optionally, a detector mount 135 may be provided to secure detector 130 in position. If present, preferably detector mount 135 allows fine adjustment to the angle of detector 130 to facilitate alignment with the transmitted beam. Detector mount 130 may include a window (not shown) that is transparent to at least the wavelengths of light emitted by laser 105. One or more interference filters (not shown) may be provided in front of detector 130, possibly as part of detector mount 135, to substantially reduce the intensity of ambient light falling on detector 130. In some embodiments additional opto-mechanical segments are present to purge the dead volumes in the absorption pathlength and/or to maintain optical features such as lenses or windows clean and scratch free and/or to manage the surface temperatures.

Gas mixture 120 may include a number of different components. These may be one or more elements, compounds, or a mixture of elements and compounds. Typical components include but are not limited to any combination of $O_2$, CO, $CO_2$, gaseous $H_2O$ and hydrocarbons such as $CH_4$. System 100 may operate to detect the presence of one or more of the components of gas mixture 120. The components to be detected will be referred to hereafter as 'measurands'. System 100 may operate to additionally or alternatively determine at least one parameter of the one or more measurands, such as the amount fraction. The determined at least one parameter may be used as an input for controlling an industrial process, possibly as feedback for a feedback loop. Each measurand has one or more absorption lines in their absorption spectrum. Absorption lines are well known to the skilled person and will not be described further here.

Detector 130 and laser 105 are communicatively coupled to an electronic detection system 140. The couplings are depicted as double headed arrows in FIG. 1. Electronic detection system 140 may be a printed circuit board (PCB) including at least one processor and a memory. Electronic detection system 140 may additionally include any combination of second harmonic detection electronics, a demodulation filter and a demodulation mixer or switch. Electronic detection system (140) may also include digital electronics to allow digital signal manipulation and processing techniques and to provide user interfaces. One skilled in the art will realise that modifications to this arrangement according to the particulars of a given system are possible.

A controller 145 is configured to control laser 105, including controlling the laser output wavelength $\lambda$. In the case where laser 105 is a TDL, the controller 145 is configured to adjust at least the diode laser bias current as a function of time and may also include temperature control of the diode laser. Further details of this adjustment are given later in this specification.

Electronic detection system 140 is also configured to receive an output signal from detector 130 that is indicative of the light incident on detector 130 as a function of time. Electronic detection system 140 is further configured to process this output signal, as described in more detail later in this specification. Electronic detection system 140 may be configured to be coupled to a display device (not shown) and may be configured to allow the display device to show one or more of the raw output from detector 130, a processed output from detector 130, a wavelength of laser 105 and a laser bias current. Other parameters may be shown in place of or in addition to any combination of these parameters. One skilled in the art will be able to construct electronic detection system 140 according to these specifications without difficulty.

Figure 2:
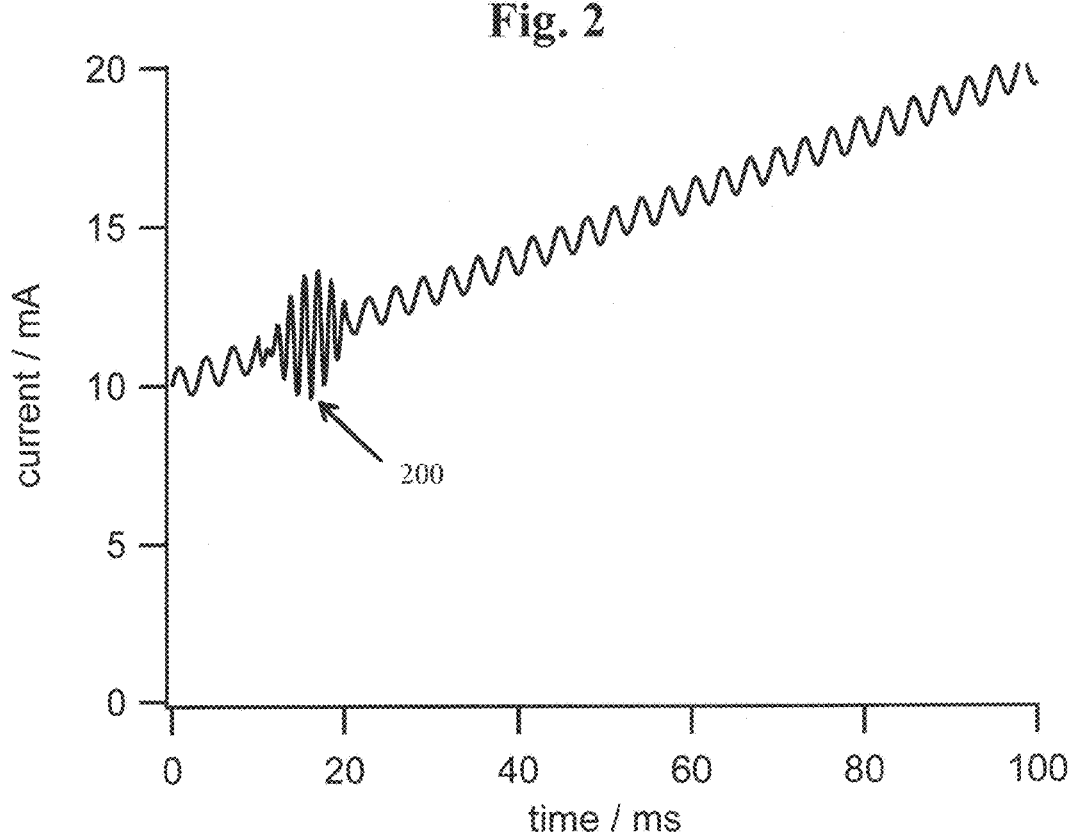
FIG. 2 is a plot showing, as a function of time, a bias current applied to a diode laser forming part of a tunable diode laser.

FIG. 2 shows, as a function of time, the bias current applied to a diode laser forming part of a tunable diode laser. The bias current is generated by the controller 145. As can be seen from FIG. 2, the bias current includes three components. The first is a low frequency linear ramp to scan the TDL output wavelength at a constant rate over one or more absorption lines of the measurand, or one or more absorption lines of each of a set of measurands.

In addition to this low frequency scan, in some embodiments a second much higher frequency bias current modulation (e.g. sinusoidal modulation) can be added. This high frequency bias current modulation is optional, and is provided to allow wavelength modulation spectroscopy to be performed (e.g. second harmonic detection).

Wavelength modulation spectroscopy is advantageously used when the laser spectroscopy is performed in a congested part of the electromagnetic spectrum; i.e. where there are many absorption lines close to one another, or even overlapping absorption lines. This is because it provides enhanced resolution that may be necessary to pick out a specific absorption line of the measurand among interfering absorption lines due to other chemical species from the background mixture. In some cases second harmonic wavelength modulation spectroscopy is preferable over direct absorption or first harmonic wavelength modulation spectroscopy because the second harmonic technique affords a greater resolution. The electronic techniques for performing first and second harmonic laser wavelength modulation spectroscopy are well established and known by those skilled in the art.

In the case of second harmonic wavelength modulation spectroscopy, in one particular embodiment electronic detection system 140 is configured to select the second harmonic signal that is generated by the response of the absorption line to the laser frequency modulation, which is then converted to a photo-current signal at twice the modulation frequency by the photo-diode (or other suitable light sensitive element) that receives the incident light. As the second harmonic signal is detected in a very narrow spectral pass band, the noise rejection is extremely high, allowing highly sensitive chemical species detection. The process is similar for other harmonic detection schemes, such as first and third harmonics, however, the signals become progressively weaker as the harmonic order increases and the second harmonic offers the best balance between signal strength, noise rejection and spectral resolution.

A third component of the bias current is an artificially generated second harmonic signal (i.e. at twice the frequency of the applied second component modulation) of typically short duration, herein referred to as the second harmonic burst 200. This second harmonic burst 200 is also applied to provide a controlled reference signal for correction of fluctuations in incident light. From a signal processing perspective, this is optimally achieved by a third component of the bias current. Here a 'short' duration is a duration that is less than the total time over which the bias current is adjusted to cause the laser to emit light across a range of wavelengths. In the embodiment of FIG. 2 the total bias current sweep time is 100 ms, and the duration of the second harmonic burst is approximately 10 ms. Hence, this example of a short duration burst signal is a burst signal duration of approximately 10% of the total bias current sweep time. Variations in this duration are of course possible, and other embodiments may include an harmonic burst having a duration of less than 10% or up to 50% or more of the total duration of the bias current sweep. The relative and absolute duration of the burst signal will depend on the measurand application and the low frequency scan range. For example, in a congested absorption spectrum, the duration of the burst signal may in practice be required to be shorter than in an identical arrangement where no background interferent is normally present. The burst duration should also ideally exceed the settling time of the demodulation filter, as this helps with reliable measurement.

An illustration of the three components of the bias current is shown below:

Bias current=Ramp Function+High Frequency Modulation+Burst Signal

The second harmonic burst 200 is applied to the tunable diode laser's bias current to provide a controlled reference signal for correction of fluctuations in incident light caused by, for example, variations in the laser power or ambient light fluctuations. In the exemplary embodiment of FIG. 2, second harmonic burst 200 begins at about 10 ms and ends at around 20 ms, but the second harmonic burst can be applied at other times during the bias current sweep. The timing and duration of the second harmonic burst is preferably chosen so that it does not overlap at all with the time window in which the output wavelength of the diode laser is tuned to an absorption line of the measurand.

In some embodiments the detected second harmonic burst signal advantageously passes directly into second harmonic detection electronics that are part of electronic detection system 140. This means that no additional signal processing electronics are required to enable processing of the burst signal, which simplifies the overall detection system.

In some embodiments, an alternative approach that achieves a similar effect is adopted. In these embodiments a burst signal is generated at a different, non-interfering frequency from the absorption modulation frequency and a separate signal processing means is used to detect this frequency component. This is less efficient than some embodiments, since it requires additional processing, but this second processing means would provide information pertaining to the laser light intensity, which could then be used in a correcting algorithm.

In many applications, the spectral region of interest may be very congested with background absorption lines and it may be difficult to find a perfectly "neutral" (zero absorption) wavelength zone (region or range). In addition, it may not be possible to eliminate all of the optical interference fringe effects, which will also be affected by mechanical vibration and temperature. In these cases, one or more of the following techniques for the burst signal may be employed in order to increase the system immunity to these effects. The following techniques involve at least one of these parameters: shape (smoothness), width (duration), amplitude or intensity (peak or dip height), location (both within the scan and as an absolute wavelength range), number of burst signals within a scan, and polarity (phase) of the second harmonic burst signal. These parameters will define the burst signal. The optimum choice of these parameters will vary between applications, laser sources and detection electronics and can be determined by calibration or calculation.

For example, the choice of wavelength selected for absorption measurements will depend on the location and strength of the absorption lines of the component of interest, the required amount fraction to be measured for a given path length and the availability and cost of commercial diode lasers. It is also desirable to have an absorption line which is relatively free of background interference. The absorption profile (lines) for a particular component may be measured in the laboratory using suitable equipment or obtained from pre-existing, privately or publicly available, databases such as HITRAN. It is a relatively straight forward task for someone skilled in the art to select an appropriate absorption line taking these considerations into account. Once the absorption line has been selected, the location and duration of the burst signal can be then be considered depending on the best "neutral" zone (free from background interference) of the nearby absorption spectrum. This will determine whether the burst signal is best located in front or behind the absorption feature during a scan, or whether it needs to be considered as a separate scan due to the localised congestion of the absorption spectrum around the absorption of the component of interest. For a difficult or congested spectrum, the number and/or polarity of the burst signal(s) can be chosen so as to optimise its application for intensity correction (i.e. in order to distinguish the burst signal from background absorption features). This is especially useful if the background absorption features may change with changing process conditions being measured.

Figure 3:
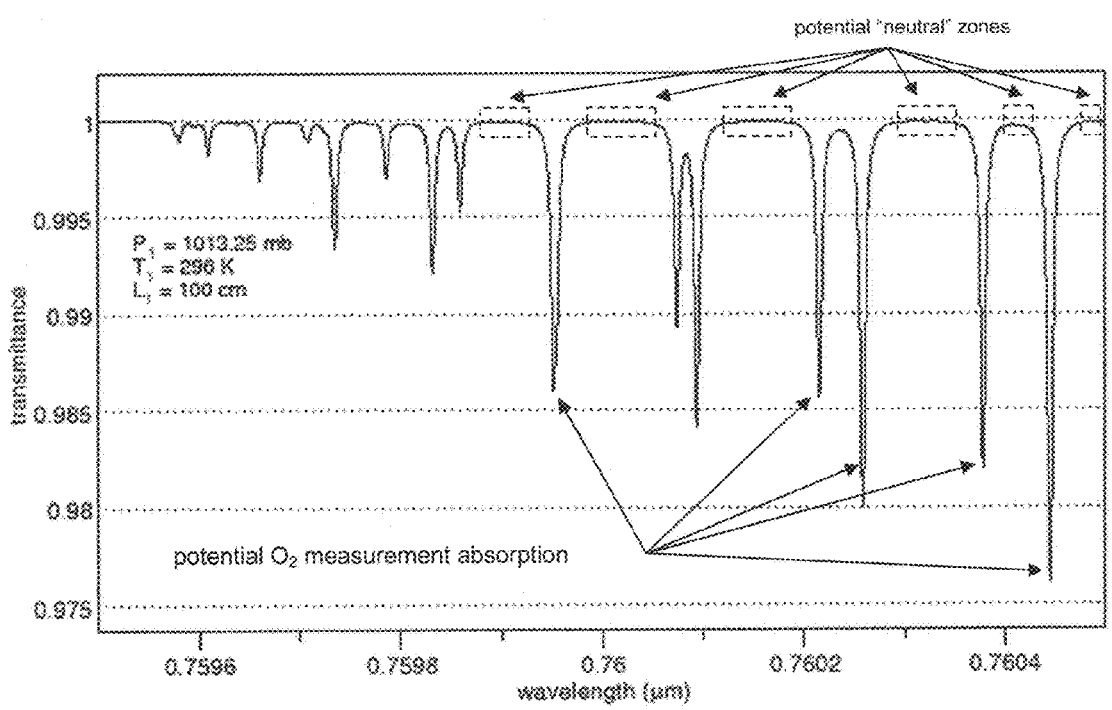
FIG. 3 is a plot showing an absorption profile of oxygen as a function of wavelength.
Figure 4:
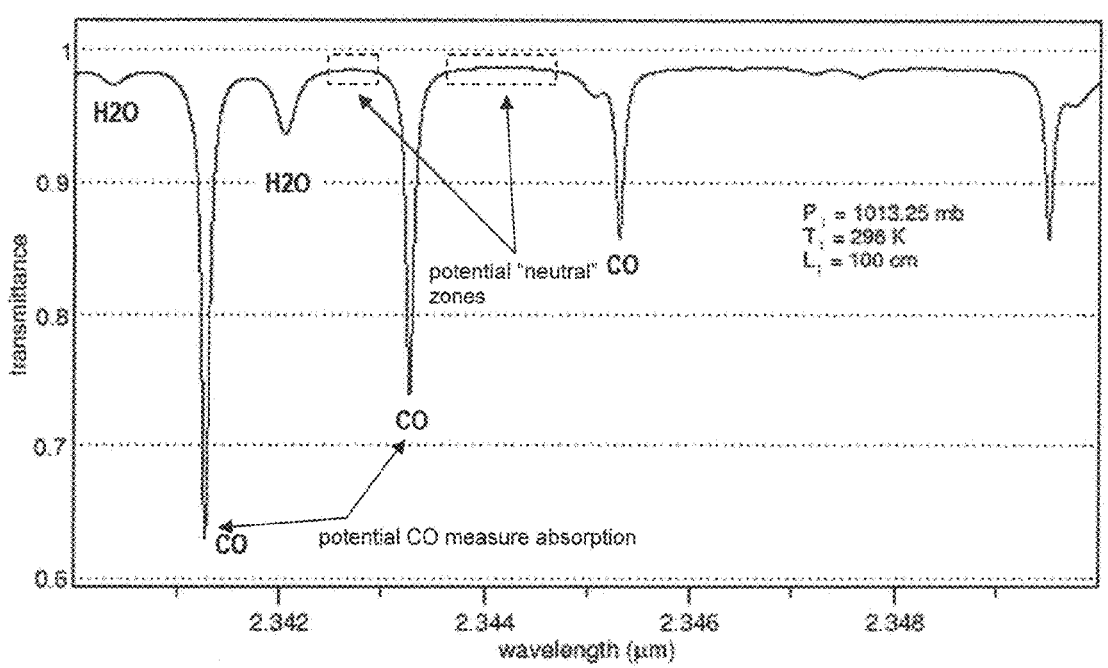
FIG. 4 is a plot showing an absorption profile of carbon monoxide and water as a function of wavelength.

The processes for selecting an appropriate measurement absorption line for a particular measurand and a "neutral" zone for an application are illustrated below for the case of a furnace application measuring oxygen and carbon monoxide using two separate diode lasers. Examples of some absorption lines for these spectra are illustrated using spectra obtained from the HITRAN 2008 database in FIG. 3 for 20% oxygen and FIG. 4 for 2% carbon monoxide and 0.7% water (multiplied one hundred times for illustration). The main gas products when a hydrocarbon fuel is burnt in air are carbon dioxide and water. Carbon monoxide may also be produced by incomplete combustion of the fuel. Under lean (low) oxygen conditions, more carbon monoxide is produced. Therefore, the measurement of carbon monoxide may be used for determining that incomplete combustion is taking place. The results of this incomplete combustion are increased fuel costs due to low furnace efficiency and increased emitted pollution. Conversely, under oxygen rich (high background oxygen) conditions, very low carbon monoxide may be present, but the furnace is still working inefficiently and will require greater fuel usage for the same net heat output since excess air is being heated by the combustion process without providing any extra fuel burn. Therefore, by measuring the amount fractions of oxygen and carbon monoxide, the furnace efficiency may be optimised and pollution minimised through manual or automatic feedback systems to adjust the fuel and/or air levels. The background interference of water lines on the oxygen spectra is low (FIG. 3), whilst that of water on the carbon monoxide spectra is much more significant (FIG. 4). The impact of the background spectra on the measurand is determined both by the relative intrinsic absorption line strengths and the amount fractions of the measurand and the background interferent species. In this application, the amount fraction carbon monoxide levels may be low, whilst the water levels may much higher. This means that water cross interference should be taken into consideration for carbon monoxide measurements. For a particular path length (100 cm for these illustrations), it is desirable that the absorption strength of the measurand line should be strong enough to give good sensitivity for the measurement and that the absorption line be separate or "clean" i.e. free from any potential interfering line. The interfering line may even be due to the measurand species itself, such as a doublet or triplet formation. Once an appropriate line has been selected, then a nearby "neutral" zone may be selected. Several potential absorption lines and "neutral" zones are suggested in FIGS. 3 and 4, and any may be chosen since the choice of line will be dependent on application and instrumentation. Note that these illustrations are for room temperature and atmospheric pressure, but equivalent spectra may be obtained for particular furnace measurement conditions. Note also that this example has shown several potential "neutral" zones. In some applications, no perfect "neutral" zone is available and so a compromise zone in terms of location relative to the absorption feature of interest and low interference error should be selected. Optical interference fringe effects may also be present even in an otherwise "neutral" zone, potentially leading to error. Due to these factors, one or more of the techniques related to the burst signal, which are described in this patent may be used to increase the accuracy of the incident light intensity correction method.

The location and duration of the burst signal may be constrained by the absorption features of the surrounding spectrum and the total desired diode laser scan duration (influenced by such factors as current tuning range available and desired scan duration for signal processing and response times). The shape or smoothness of the burst signal is also chosen so as to avoid inducing any ringing in the detector electrics. The required shape of the burst signal may be application dependent (for example the rate of change of amplitude or smoothness during the burst signal may be constrained in a congested spectrum) and instrumentation dependent (such as dependent on the detector electronics). The desired shape profile (window) can be tested experimentally to confirm that the processed burst signal has the desired shape. These burst signal parameters will now be treated separately in more detail in the following paragraphs.

As shown by way of example in FIG. 2, the second harmonic burst signal is optimally a smoothly tapering signal modulation that avoids sharp signal transitions at the start or end of the burst. This is achieved in a first embodiment by the burst signal modulation (e.g. sinusoidal modulation) of the tunable diode laser's bias current employing a smooth window function to shape the burst signal. This window function controls ramping up and down of the burst signal amplitude and/or controls the phase, such that sudden signal transitions are avoided. In a first embodiment, a tapered cosine (or 'Tukey') window function is used to modulate the amplitude of the bias current, but other smooth window functions may be used. These smooth window functions may be any of a Planck-taper window, Kaiser-Bessel window, Hamming window, Harming window, Blackman window or a triangular window if the gradient is not too high) or any tapering window function that is sufficiently smooth to avoid initiating a "ringing" impulse response in the detection electronics (see below). The window function may also be referred to as an 'envelope function'. By controlling the parameters of the window function, it is possible to achieve a burst signal shape that combines smooth start and end transitions with a portion of the signal that has a stable amplitude. The smoothed signal edges and uninterrupted bias current help to avoid ohmic heating of the diode laser and to avoid "ringing" at the detector electronics; whereas the stable amplitude part of the burst signal ensures that the burst signal has a shape that is easy to differentiate from any absorption lines and allows instantaneous fluctuations to be detected.

An illustration of a burst signal shape is given below for a second harmonic embodiment:

Burst Signal=Second Harmonic Modulation×Window Function

Figure 5:
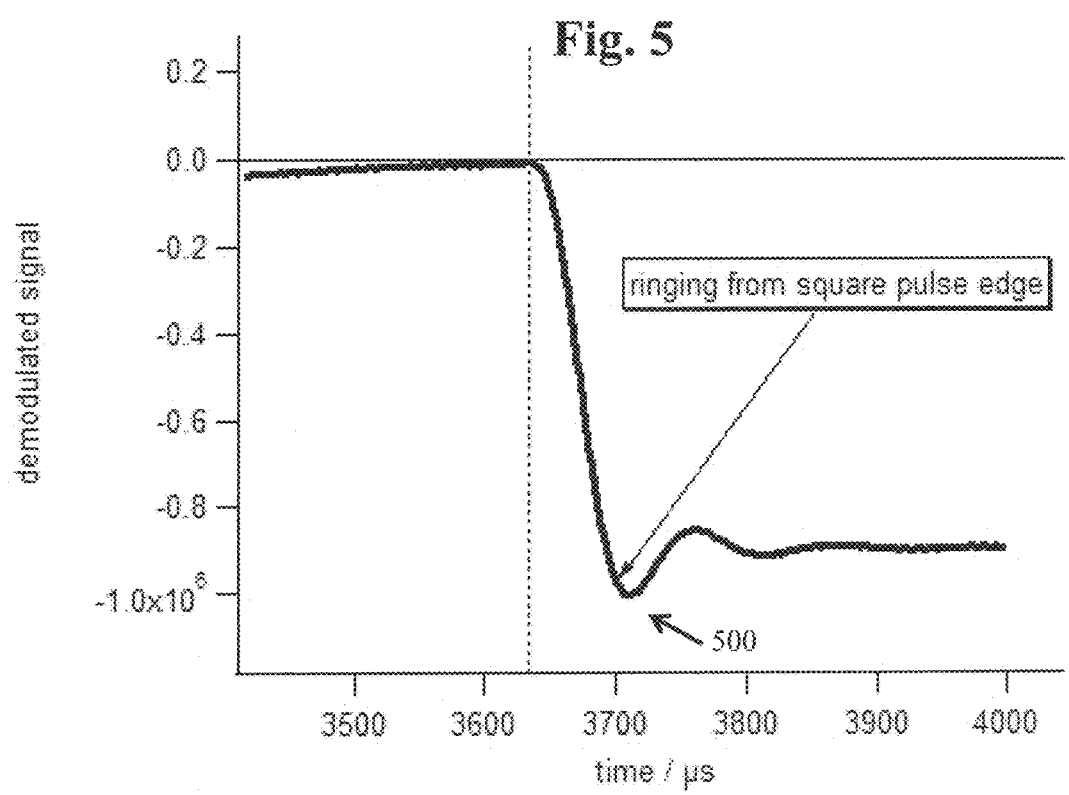
FIG. 5 is a schematic diagram showing ringing effects that can be caused by a square wave burst signal.

Use of a smooth window function to control modulation of the tunable diode laser's bias current is desirable to avoid sharp transitions in the detected signal that would excite an impulse response of the wavelength modulation spectroscopy system. This impulse response can result from a dynamic response of the demodulation filter that follows the demodulation mixer or switch. Excitation of the impulse response by a sharp signal edge often results in a signal distortion that decays periodically over time—termed "ringing". The use of a square pulse for the second harmonic burst would be likely to excite such unwanted impulses, resulting in a demodulated signal such as shown in FIG. 5. In this figure, the ringing behaviour is clearly visible in the portion of the demodulated signal labelled 500 at approximately 3700 μs to 3800 μs. This is problematic because the decaying periodic feature could be mistaken for part of a spectroscopic signal, when it is in fact merely an artefact of the signal processing.

An advantage gained by introducing the smooth window function is that the amplitude of the second harmonic burst can then be made relatively large in order to significantly improve the signal to noise ratio without "ringing". Here 'large' is defined relative to the average amplitude of the unmodulated bias current that would otherwise have been applied during the time interval in which the second harmonic burst is superimposed on the bias current. In the exemplary embodiment of FIG. 2 the peak-to-peak amplitude of the second harmonic burst is approximately 4 mλ and the average amplitude of the unmodulated bias current during the 10 to 20 ms interval is approximately 12 mA. The peak-to-peals amplitude of the second harmonic burst is therefore approximately one third of the average unmodulated bias current. Variations in this amplitude are of course possible, and other embodiments may have a window function that results in a peak-to-peak amplitude of the second harmonic burst being less that 10% or more than 50% of the average amplitude of the unmodified bias current applied during the time interval over which the second harmonic burst is applied.

In any case, the smooth window function should preferably produce a second harmonic burst that has a sufficiently large amplitude to be readily distinguishable from both the unmodulated bias current and any high frequency modulation that may also be applied to the bias current. In some preferred embodiments, the window function is selected so that the shape of the burst feature is significantly different from that associated with a natural absorption line (e.g. the burst feature should not resemble Lorentzian, Gaussian or Voigt waveforms) or lines (e.g. doublet or triplet absorption lines) or optical interference fringes (e.g. not sinusoidal). In some embodiments, the burst signal may also include a central plateau feature. In some embodiments, the amplitude of the burst signal is made so large so that small fluctuations are of less significance.

Another advantage of using a smooth window function is that the demodulation filter speed can be made fast to preserve fine spectral features of the measurand signal, which enables accurate determination of parameters such as the line width.

In some embodiments, the burst feature occurs within a scan window including the absorption feature or features of interest. In other embodiments the burst feature occurs in a separate scan or scans, closely interleaved in time with the absorption scan of interest. In a congested absorption spectrum, it is useful to have the burst signal located in a neutral zone that is separated from the measurand absorption feature, but without having to scan through multiple absorption interference lines in between the burst feature and the measurand absorption feature, which could cause unwanted time delays and/or potential signal processing errors. Additionally, this allows a greater number of averaging scans for the (typically smaller) measurand signal compared to the (typically larger) burst signal, thus allowing for lowered background noise and hence enhanced signal accuracy for the same total averaging time duration compared to having equal numbers of averaging scans.

As well as the amplitude and smooth transitions of the burst signal, the width of the burst can also be optimised, for example by selection of the window function. In some embodiments, the width and/or amplitude of the burst is chosen so as be significantly greater than any predicted baseline fluctuations due to background absorption or optical fringe interference. This will advantageously minimise the influence of any changes of these background effects on the burst signal. An ultimate limitation to the amplitude is the avoidance of saturation of the signal processing chain. The width of the burst is preferably chosen to be less than the period of the TDL scan rate.

In some embodiments individual or multiple second harmonic bursts (including of different shapes and/or widths/amplitudes) are located before and/or after the absorption feature of interest, dependent on the best location for minimum background interference. Each may have the same window function, or a different window function may be used for each burst. Weighted or unweighted averaging and/or sampling techniques can then be employed to decrease the influence of random or multiple potential absorptions or optical interference fringes.

In some embodiments the location of the single burst or locations of multiple bursts relative to the absorption feature of interest is varied between cycles within a defined sub-window, such that the burst does not impinge on the absorption area of interest, but highlights if interference is taking place through changes in the measured light intensity. This interference can then be minimised through signal averaging techniques over the different locations. Alternatively, the lowest interference location or locations may be chosen as the polling point(s) (preferred light intensity reference value (s)) for any given total cycle period of all of the different locations for systematic interference.

The second harmonic signal is preferably detected at an optimised, fixed phase. The second harmonic burst shape can therefore be generated by amplitude modulating the laser output at fixed, synchronised phase with the processed second harmonic signal. However, in some embodiments, phase modulating the laser output at a fixed amplitude, or a simultaneous combination of modulating the phase and amplitude, is utilised to obtain a smooth second harmonic signal modulation. Phase modulation to control generation of a suitable burst signal has an advantage over pure amplitude modulation in that there is an improved signal to noise ratio in comparison with pure amplitude modulation at fixed phase (since, in order to have the same relative noise effect, the noise would have to be phase correlated with the laser output, which is unlikely to be the case). Phase modulation of the input signal works well because the demodulation is phase sensitive. In particular the amplitude of the demodulated signal is dependent on the phase angle between the modulation signal and the reference signal used to demodulate the signal.

In some embodiments, the input signal modulation is chosen to generate an inverted but signal relative to any absorption feature or features. This advantageously means that the burst will not be mistaken for an absorption feature or features.

The phase dependence of second harmonic detection derives from the lock-in detection technique used to derive the second harmonic signal from the other frequencies present. The typical dependence is illustrated in the equation below. The demodulated output signal $V_b(t)$ with time t is proportional to the cosine of the phase angle $\phi$ as shown by equation 3. By changing the reference phase angle, the amplitude of the processed signal may be decreased, increased or inverted.

$$V_b(t) \propto Cos\phi \quad [3]$$

Figure 6:
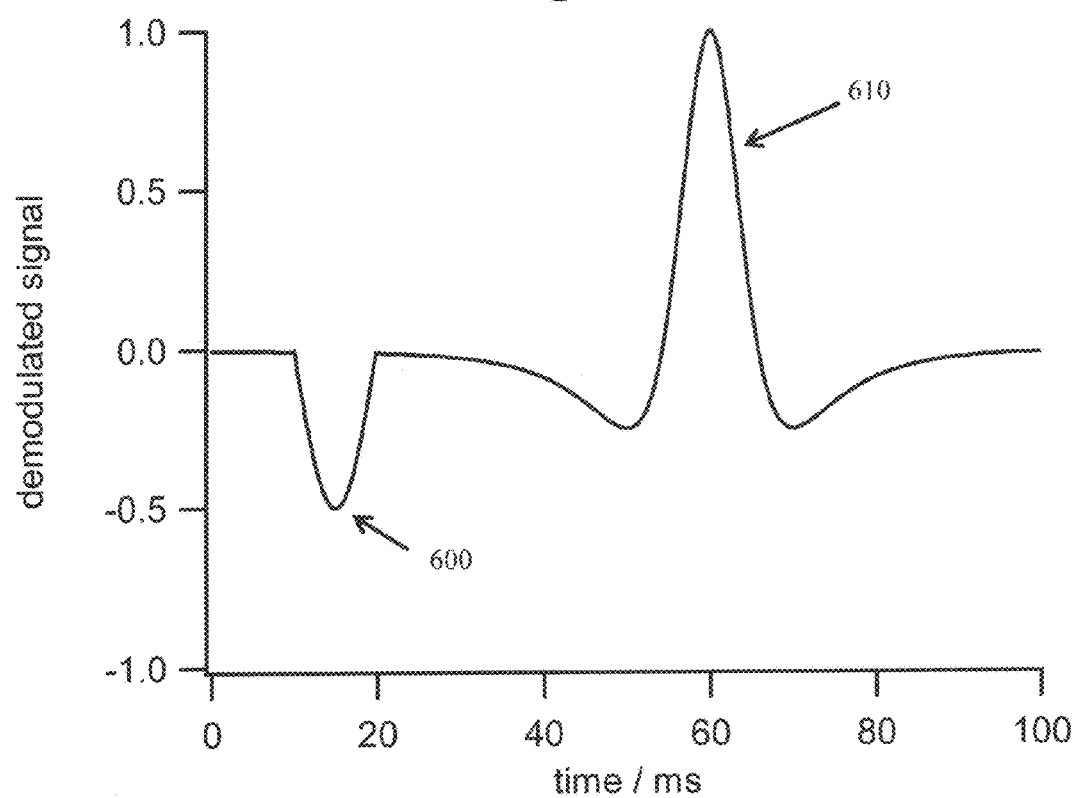
FIG. 6 is a schematic diagram showing an exemplary demodulated signal according to embodiments described herein.

A resulting demodulated signal produced by the second harmonic detection electronics of electronic detection system 140 is shown in FIG. 6. A demodulated signal of this type can be obtained by either an amplitude modulated or phase modulated second harmonic burst according to previously described embodiments. The second harmonic burst produces a smoothed pulse reference signal 600 for the incident light correction. In the exemplary embodiment of FIG. 6, the smoothed pulse reference signal 600 is shown from approximately 10 ms to 20 ms. This feature clearly does not exhibit ringing behaviour. Also shown in FIG. 6 for reference purposes is a second harmonic absorption line signal 610 produced by a measurand. As is clear from FIG. 4, reference signal 600 does not overlap with absorption line signal 610.

Reference signal 600 can be used for the incident light correction of variations in the optical power incident on detector 130 that are due to e.g. variations in laser output power and/or variations in ambient light levels. The phase of the second harmonic burst may be chosen to produce either a negative pulse or a positive one, depending on what best suits the downstream signal processing algorithms that deduce the amount fraction of measurand from the second harmonic absorption line signal 610. FIG. 6 shows a pulse of negative polarity.

The magnitude of the reference signal 600 is directly proportional to the amount of incident light $I_0(J)$ and the magnitude of the second harmonic absorption line shape 610 is directly proportional to both the amount of incident light and amount of measurand. Therefore the magnitude of second harmonic absorption line shape 610 can be corrected for the incident light fluctuation using the relationship of equation 4:

$$A_{corr}(v) = \frac{A_{meas}(v) I_{0,ref}(v)}{I_0(v)} \quad [4]$$

where $A_{corr}(v)$ is the amplitude of the corrected second harmonic absorption signal at laser frequency v, $A_{meas}(v)$ is the amplitude of the measured second harmonic absorption signal, $I_0(v)$ is the amount of incident light deduced from the reference signal 600 produced by the second harmonic burst signal and $I_{0,ref}(v)$ is the reference amount of incident light corresponding to an un-obscured optical path i.e. a transmission factor of one hundred percent.

Because the second harmonic burst signal is a unique feature of the laser beam, it is clearly distinguished from detector signals caused by ambient light. It is also readily distinguished from the so-called 'dark current' signal of a photodetector, which creates a dark current offset as is known to a skilled person. This means that, unlike prior art methods for dealing with these sources of error, there is no need to temporarily turn off the diode laser for this purpose, thus avoiding ohmic heating perturbation on the laser light source. This results in improved measurement accuracy, particularly when a TDL is being used.

A number of mathematical methods may be used to obtain the magnitude of the reference signal 600 caused by the second harmonic burst signal and thereby deduce the effects of ambient light and obscuration on the amount of incident light $I_0(v)$. However, it is preferable to choose a method that offers best immunity from noise and baseline variations, and, in particular, from residual selective absorption by the measurand or background chemical species. For this reason, although some embodiments may use the simple method of using the peak height (or dip) of the reference signal 600, this is not always the best choice.

A preferred method involves integrating the reference signal 600 to obtain the enclosed area from the nominal base line, which has the effect of filtering the higher frequency noise. There may also be residual feed through of the first or second harmonic laser modulation signals after the demodulation filter, as, in practice, one cannot achieve an ideal "brick wall" filter to reject the modulation signal completely or without severe phase delay penalty.

By careful choice of the integration bounds, so that is the region being integrated over is an integer multiple of the modulation signal period, the integration also acts as a comb filter within a digital signal processing system. This advantageously greatly suppresses any modulation feed through.

Figure 7:
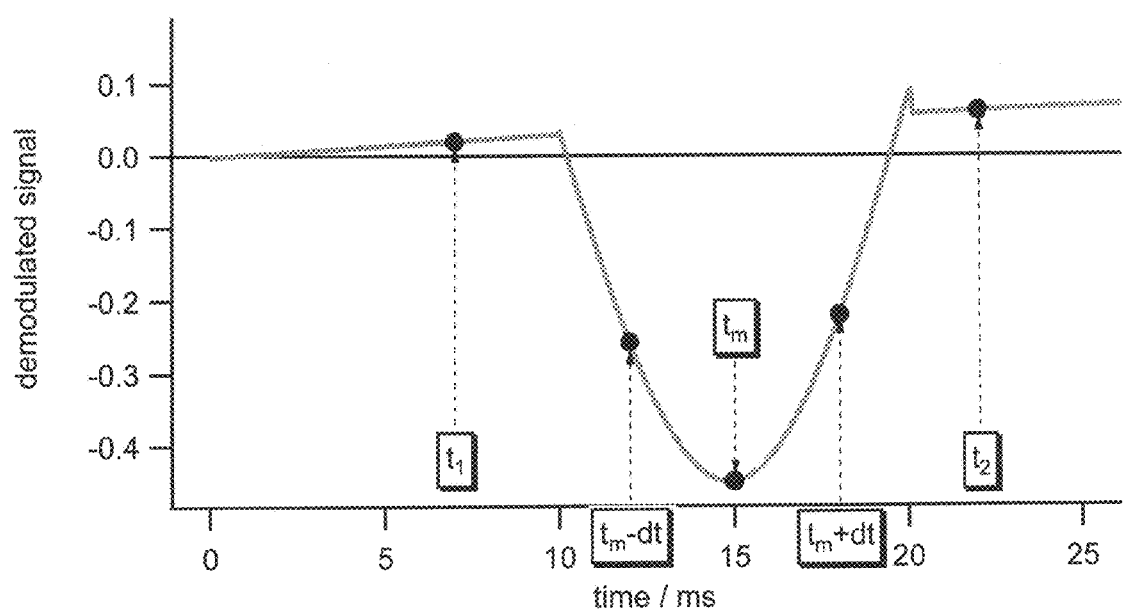
FIG. 7 is a schematic diagram illustrating baseline ramp correction of a TDL driving current.

Low frequency noise and baseline variations can be rejected by subtracting the baseline ramp in the vicinity of the reference signal 600 using a multi-point point correction. A two point correction is normally adequate, since the laser frequency scan range over the pulse width is sufficiently small that a linear approximation may be used. As shown in FIG. 7, two points $t_1$ and $t_2$ that lie just outside the reference signal 600 may be used for the base line ramp corrections, which occur at times $t_1$ and $t_2$.

The baseline ramp function r(t) may in some instances be approximated by the linear form shown in equation 5:

$$r(t) = m_{t+b} \quad [5]$$

where the slope m and the coefficient b are given by equation 6 and equation 7 respectively:

$$m = \frac{S(t_2) - S[(t]_1)}{t_2 - t_1} \quad [6]$$

$$b = S(t_1) - t_1 \frac{S(t_2) - S[(t]_1)}{t_2 - t_1} \quad [7]$$

The final integration of the reference signal 600 is given by equation 8, where $t_1$ and $t_2$ are the integration bounds, S(t) is the reference signal 600 at time t, r(t) is the base line ramp function from equation 5 and v is the optical frequency at which the second harmonic burst occurs, $$I_0(v) = -\int_{t_1}^{t_2} [S(t) - r(t)] \partial t \quad [8]$$

In embodiments where the second harmonic burst is a symmetric function, it is possible to use two points within the reference signal 600 for the baseline ramp correction, where the two times $t_m-dt$ and $t_m+dt$ are equally spaced by dt from either side of the reference signal mid-point time $t_m$, as shown in FIG. 7 also. In this specific case, the slope m and coefficient b are given by equation 9 and equation 10 respectively. This method is advantageous if the absorption spectrum is highly congested, where finding neutral points just outside the reference burst signal to define the base line ramp may become difficult.

$$m = \frac{S(t_m + dt) - S[(t]_m - dt)}{2dt} \quad [9]$$

$$b = S(t_m - dt) - (t_m - dt)\left[\frac{S(t_m + dt) - S(t_m - dt)}{2dt}\right] \quad [10]$$

The second harmonic burst can be located anywhere within the laser frequency scan, but preferably is not too close to the measurand absorption line. More preferably the second harmonic burst is in a neutral part of the spectrum that is free from any strong selective absorption by interfering background chemical species. Since the second harmonic burst is of a short duration compared to the duration of the laser frequency scan, it can be located with a high degree of precision, which is particularly useful when measuring in a congested spectrum, such as that shown in FIG. 4.

Figure 8:
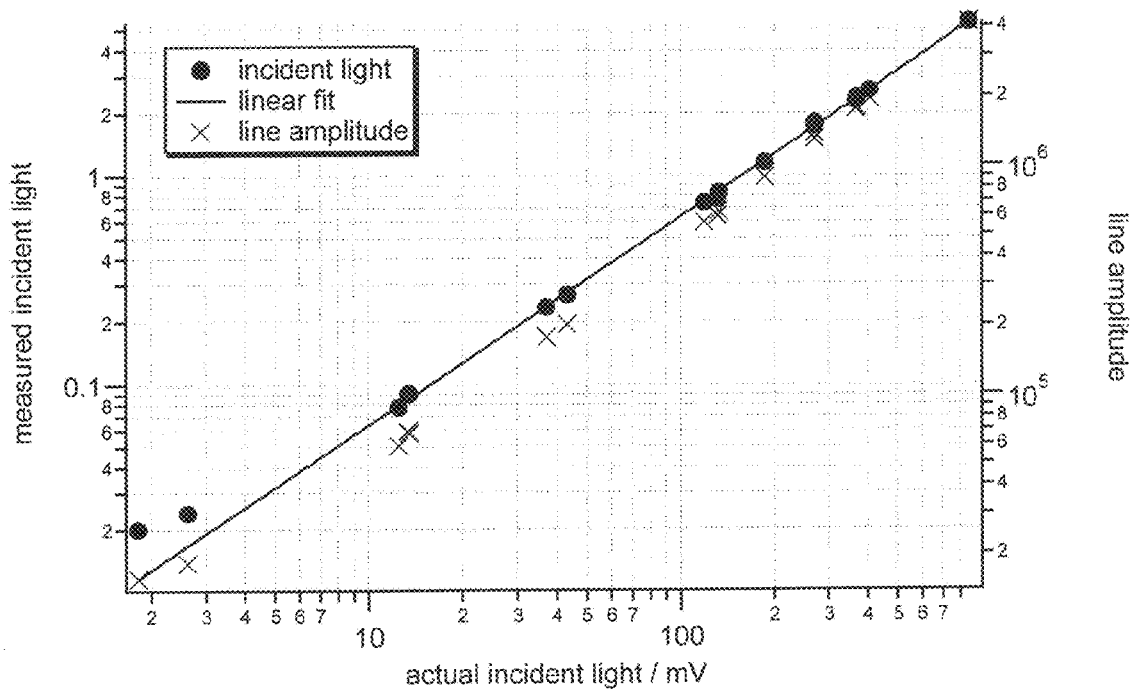
FIG. 8 is a logarithmic plot showing ambient light correction according to embodiments described herein in operation over several orders of magnitude of ambient light intensity.

FIG. 8 is a logarithmic plot that shows measurements of the incident light correction using the second harmonic burst method of embodiments described above. The left-hand vertical was indicates the amount of incident light deduced from integration of reference signal 600 using equation 8 and the horizontal axis indicates the actual amount of incident light $I_0(v)$. The solid circles are data points generated by integration of the reference signal and the solid line is a trend line through those data points. As is clear from FIG. 8, there is direct agreement between the two quantities that extends over several orders of magnitude, demonstrating the ability of embodiments described herein to accurately determine incident light levels.

The second harmonic absorption line amplitude $A_{meas}(v)$ is indicated on the right-hand vertical axis, and is shown by the data points represented by crosses. It is clear from FIG. 8 that the direct relationship between this quantity and the actual amount of incident light $I_0(v)$ as indicated by equation 3 holds true.

Figure 9:
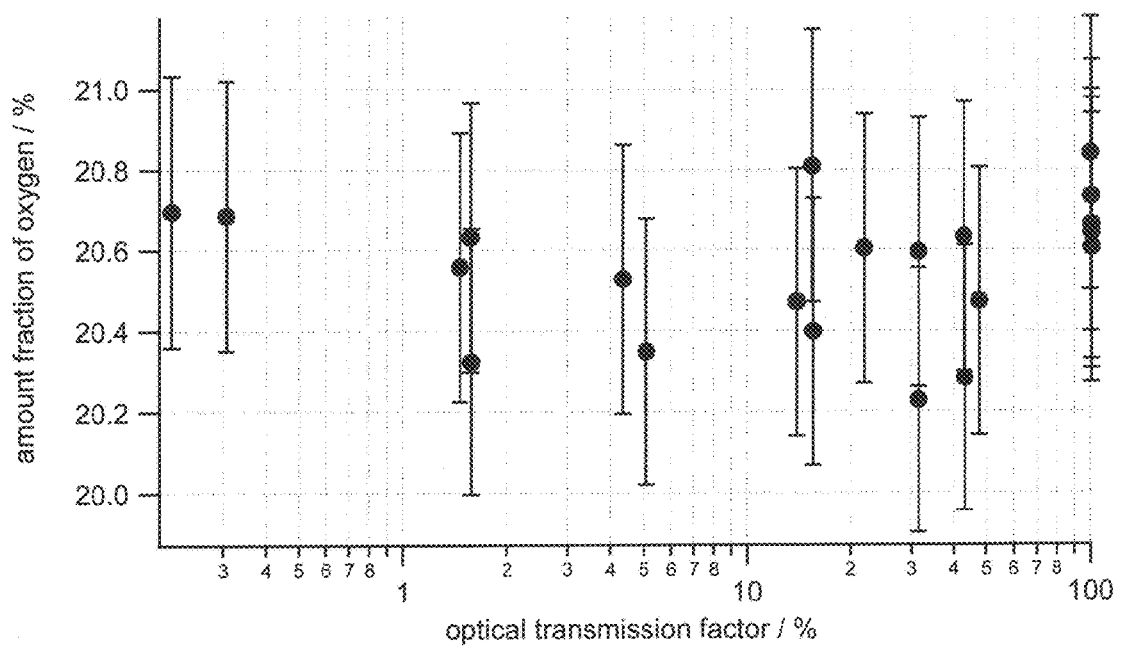
FIG. 9 is a plot showing the detection of atmospheric molecular oxygen according to embodiments described herein.

A demonstration of the incident light correction achieved by embodiments described herein using the detection of atmospheric molecular oxygen by second harmonic wavelength modulation spectroscopy is shown in FIG. 9 for a large range of optical transmission factors. These were simulated using sets of neutral density filters in the measurement beam path of the test apparatus. The amount fraction of molecular oxygen is adequately corrected for optical transmission factors as low as 0.25 percent, demonstrating the ability of embodiments to accurately determine a measurand concentration across a wide range of obscuration conditions. In addition, FIG. 9 shows that embodiments described herein are able to account for variations in laser output power that would effectively manifest as a short-term change in the optical transmission factor of a gas mixture.

In order to achieve the wide dynamic range of incident light correction as shown by the results in FIGS. 8 and 9, it is necessary to prevent the dynamic saturation of the photo diode or other light sensitive element that may be used. The dynamic saturation refers to the detector response at the laser modulation frequency and its harmonics, which is different from the saturation caused by the average amount of (or continuous wave) incident light that those skilled in the art are normally familiar with. With diffraction limited optics that are commonly used in front of photo diodes to improve their field of view, the dynamic saturation limit can be reached with laser beam powers less than one milliwatt. The most significant effect of approaching the dynamic saturation limit is that it alters the phase response of the second harmonic signal from the measurand absorption line, which changes the apparent line amplitude detected by a demodulation system that is normally configured for a fixed phase relationship. Consequently, the relationship of equation 4 becomes invalid due to the non-linear response caused by the dynamic saturation effect.

Figure 10:
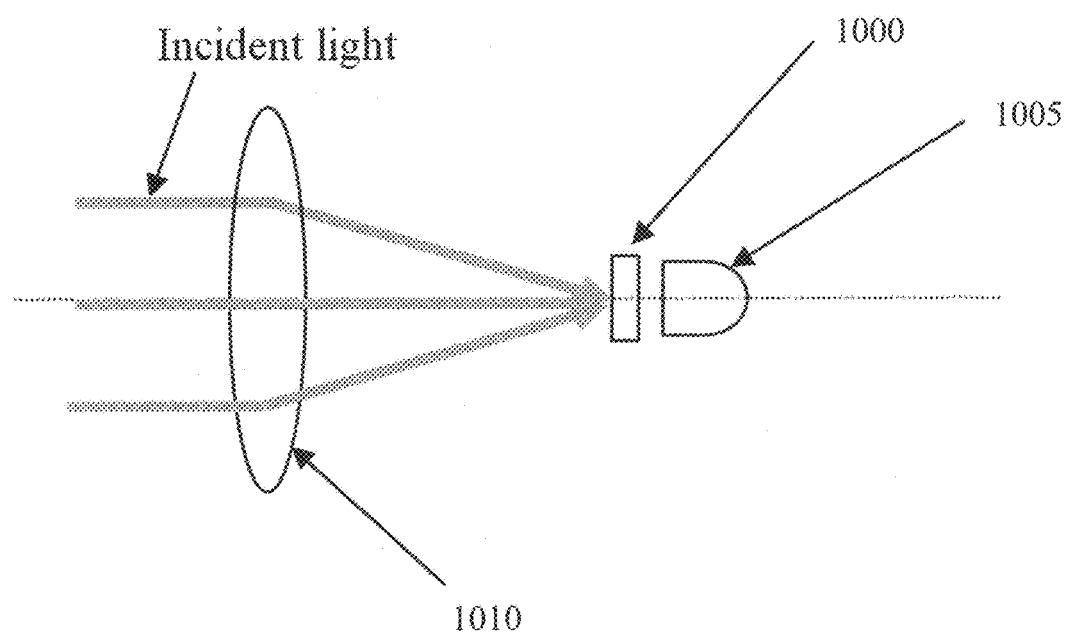
FIG. 10 is a schematic diagram of a photo detector system including a diffuser.

Optical techniques to reduce the irradiance level on the photo diode are known to those skilled in the art. However, the inventors of the present invention have determined that these techniques may be effective and practical for preventing dynamic saturation of the photo diode and this may include the provision of a diffusing element in front of the photo diode or to offset the photo diode from the focal plane of the collection lens if one is used in front of the photo diode. Using a diffusing element, however, provides the greatest dynamic range for incident light levels and does not diminish the field of view of the photo detector system. An example of a photo detector system with a diffuser 1000, which may be used to implement the present invention, is shown by the diagram in FIG. 10. As can be seen from FIG. 10, optical diffuser 1000 is located substantially in front of the photo diode 1005 and the laser diode. Optionally, a lens 1010 may be provided in the beam path between the diode laser and diffuser 1000 to focus the light onto diffuser 1000.

In the above, embodiments have been shown to correct for the effect of laser light intensity fluctuations as applied to a single absorption line of a single chemical species. However, embodiments described herein could equally well be applied to multiple lines of the same chemical species and/or single or multiple lines of several chemical species occurring within a single or multiple sweeps.

In an alternative embodiment, the diode laser is modulated by a separate device in order to generate the second harmonic burst signal. This separate device may be an electro-optical modulator, an acousto-optic modulator, a liquid crystal optical modulator, a micro electro-mechanical system (MEMS) based variable optical attenuator, an interferometric based variable optical attenuator or any other suitable means synchronised to the demodulating detector. This may be a preferred variation of the technique if the modulation frequency is too high for bias current modulation or if the corresponding RAM cannot be tolerated.

In another alternative embodiment, the second harmonic burst signal is generated by a separate light source at a substantially different wavelength than the diode laser used, synchronised with the absorption laser, so that interference from the background species absorption is greatly reduced. The separate light source may be another diode laser or a light emitting diode (LED), which has an emission wavelength that can be detected by the same or separate detector (e.g. photo-diode) used for the wavelength modulation spectroscopy. A separate LED source has the advantage of not being subject to optical fringe interference due to its lack of coherence compared to a diode laser. The separate light source and, in some embodiments, separate detector are substantially co-located with the absorption diode laser and detector in order to maintain an equivalent optical path.

However, the use of the same signal processing chain for the burst signal and the wavelength modulated signal used for absorption measurement is advantageous for other reasons. Firstly, it is efficient to make use of a single signal processing chain (electronics and software) and, secondly, any signal processing errors that occur are common mode errors for both the wavelength modulation signal and the applied burst signal. These are advantages of embodiments in which the burst signal modulation (that is used for error correction) is applied to the same input control signal of the tunable diode laser as the wavelength modulation (that is used for measurand detection and measurement).

Various solutions according to the invention are thus able to compensate for intensity fluctuations and signal processing instrumentation problems for improved spectroscopic measurement accuracy.

In view of the above discussion, it will be evident to a person skilled in the art that embodiments described herein offer many advantages. One such advantage is that the limitations caused by non-linear perturbations that are inherent in tunable diode laser spectroscopy systems, such as the ohmic heating perturbation and signal processing instabilities, are overcome. Another advantage is that the residual background absorption interference or optical fringe interference for the correction of instantaneous or quasi-instantaneous incident light fluctuations in wavelength modulation spectroscopy can be accounted for, resulting in improved quantification of one or more measurands. In addition, it will be evident to a person skilled in the art, that although this method has been illustrated with particular reference to second harmonic wavelength modulation spectroscopy, it could equally be applied to other absorption spectroscopy techniques such as frequency modulation spectroscopy (FMS) or direct absorption spectroscopy (DAS). It can also be applied to measurements in media other than gas (e.g. liquid or solid) or to a mixture of media (e.g. a solid and/or liquid species in a gas).

The invention can be used in calibration of a laser absorption spectroscopy system, by varying the input parameters of a window function that controls the tapering of signal transitions to achieve an optimal burst signal shape that avoids ohmic heating effects and oscillating amplitude or phase fluctuations in the measured burst signal. This calibration capability allows the same controller to be used with different combinations of tunable diode laser and detector electronics, as the input signals can be adjusted until signal processing errors are mitigated. This calibration step can include identification of a neutral part of the scanned wavelength spectrum in order to choose an optimal location of the burst signal as well as control of the burst signal shape. This calibration step may be implemented manually or through the use of an automated system.

Figure 11:
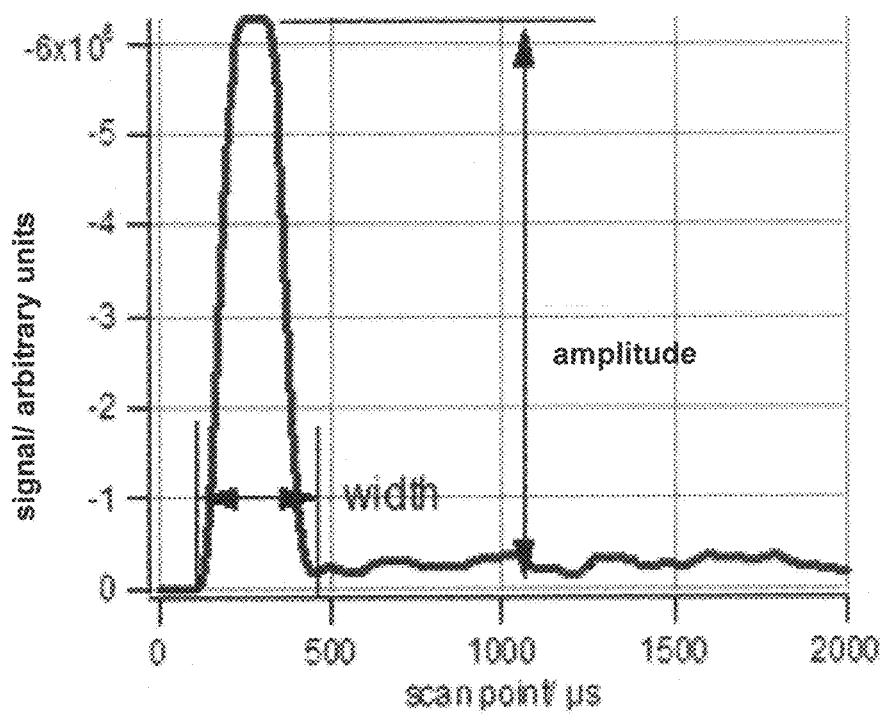
FIG. 11 is a schematic diagram of a calibration burst signal.

The following is an example of a procedure used to set up a burst signal for intensity fluctuation compensation (see FIG. 11). This example is purely illustrative and the exact procedure used in any individual case will depend on the instrumentation and application.

Procedure:
1. Choose diode laser and absorption analyser as appropriate for desired gas measurement.
2. Select burst signal shape (e.g. Tukey window function).
3. Set amplitude (peak height) of burst signal to 90% of the full scale range of the analogue to digital converter (ADC) input. This is to obtain approximately the highest practical signal to noise ratio possible for the optical transmission compensation.
4. Set burst width to 20% of the laser wavelength scan range. This is to allow sufficient space for both the burst signal and absorption profile to be measured in a single scan,
5. Set position to within the first ¼ section or last ¼ section of the laser wavelength scan where there is no gas absorption response, including background gas species. This leaves the middle zone for the measurement of the absorption feature of interest.

This sequence of steps can be followed by detecting the burst signal and comparing the detected burst signal with the modulation burst signal to identify signal processing anomalies, and then modifying the modulation burst signal to reduce the anomalies.

In addition to the embodiments described above and claimed in the appended claims, the following is a list of additional embodiments that each may serve as the basis for additional claims in this application or a divisional application.

Embodiment 1: A method of correcting for the effects of intensity fluctuations of incident light within an absorption spectroscopy system, comprising the steps of:
controlling a light source to emit a wavelength modulated beam of light;
applying at least one modulation burst signal to modulate the wavelength modulated beam and/or to modulate a separate beam synchronised with the wavelength modulated beam, which at least one modulation burst signal is a tapering signal modulation;
detecting the modulated beam or beams of light after transmission through a sample medium;
processing the detected beam or beams to obtain at least one detected burst signal and to measure absorption effects of one or more measurands, wherein the processing includes comparing the at least one detected burst signal with the applied at least one modulation burst signal to determine intensity fluctuations of the incident light that are separate from absorption effects of the measurand(s), and correcting for the effects of the determined intensity fluctuations for increased accuracy of measurement of the absorption effects of the measurand(s).

Embodiment 2: The method of embodiment 1 including selecting at least one wavelength zone location and/or duration for the at least one burst signal to isolate the burst signal from a measured absorption line of the measurand(s).

Embodiment 3: The method of embodiment 1 or 2, wherein the light source is a tunable diode laser and the laser's bias current is repeatedly scanned across a range of values at a scan rate having a period T, for wavelength modulation of the laser's beam of light, and wherein the duration of the burst signal is less than the period T.

Embodiment 4: The method of any of embodiments 1-3, wherein the modulated beam is detected by a photodetector and the processing further comprises:
processing an output signal from a photodetector to obtain a reference signal proportional to the detected burst signal; and
using the reference signal to produce a corrected signal that is proportional to the concentration of one of the one or more measurand species.

Embodiment 5. The method of any one of embodiments 1 to 4, wherein the burst signal is amplitude modulated at fixed phase.

Embodiment 6. The method of any one of embodiments 1 to 4, wherein the burst signal is phase modulated at fixed amplitude.

Embodiment 7. The method of any one of claims 1 to 4, wherein the burst signal is both phase and amplitude modulated.

Embodiment 8. The method of any one of the preceding embodiments 1 to 5, wherein the frequency of the burst signal is chosen to be equal to an harmonic frequency of the light source modulation frequency used for the spectroscopic measurement of the absorption effects of at least one measurand.

Embodiment 9. The method of any one of embodiments 4 to 8, wherein the processing further includes integrating the reference signal over a period equal to an integer number of laser modulation frequency periods.

Embodiment 10. The method of embodiment 9, wherein a baseline ramp function is subtracted from the reference signal to correct for selective residual absorption of the measurand and any background chemical species.

Embodiment 11. The method of embodiment 6 where the frequency of the burst signal is equal to the second harmonic of the laser modulation frequency used for spectroscopic measurement of the absorption effects of at least one measurand.

Embodiment 12. The method of any one of embodiments 1 to 11, wherein the light source is a diode laser and the step of applying a modulation burst signal includes modulating the bias current of the diode laser to produce the burst signal.

Embodiment 13. The method of any one of embodiments 1 to 11, wherein the detecting and processing steps are carried out by a demodulating detector, and the burst signal is applied using an external modulation device synchronised to the demodulating detector.

Embodiment 14. The method of any one of embodiments 1 to 11, wherein the detecting and processing steps are carried out by a demodulating detector, and the burst signal is applied using a secondary diode laser or light emitting diode synchronised to the demodulating detector.

Embodiment 15. The method of embodiment 6 or 7, wherein phase modulation is used to invert the burst signal.

Embodiment 16. The method according to any one of embodiments 1 to 15, wherein a single absorption line of at least one measurand species is corrected for laser light intensity variations.

Embodiment 17. The method according to any one of embodiments 1 to 15, wherein multiple absorption lines of at least one chemical species are corrected for laser light intensity variations.

Embodiment 18. The method of any one of the embodiments 1 to 17, wherein the shape of the tapering signal modulation is chosen to be different from any naturally occurring absorption shape or optical interference fringe effect.

Embodiment 19. The method of any one of the preceding embodiments 1 to 18, wherein at least one of the amplitude and the width of the burst signal is chosen to be substantially larger than any expected natural background fluctuation.

Embodiment 20. The method according to any one of the preceding embodiments 1 to 19, wherein multiple burst signals are used in order to determine the light intensity fluctuations.

Embodiment 21. The method of embodiment 20, wherein averaging of the measured light intensity is use to minimise a correction error.

Embodiment 22. The method of embodiment 20 or embodiment 21, wherein the corrected light intensity is calculated based on a selected subset of burst signals, the subset including one or more of the multiple burst signals.

Embodiment 23. The method of embodiment 3, wherein the position of at least one burst signal is varied between scan cycles.

Embodiment 24. The method of any one of embodiments 1 to 23, wherein the laser light source is a tunable diode laser and the laser's bias current is ramped up and down across a range of values to vary the laser's output beam across a range of wavelengths; and wherein the method further comprises identifying absorption wavelengths of gases in the sample gas and choosing the location of the modulation burst signal within the wavelength range to avoid the identified absorption wavelengths.

Embodiment 25. The method of any one of embodiments 1 to 24, wherein the tapering signal modulation of the burst signal is generated using a window function.

Embodiment 26. The method of embodiment 25, wherein the window function is one of a Tukey window function, a Planck-taper window function, a Kaiser-Bessel window function, a Hamming window function, a Hanning window function, a Blackman window function or a triangular window function.

Embodiment 27. The method of any one of the embodiments 1 to 26, wherein the burst signal is inverted with respect to at least one absorption feature of the one or more measurand species.

Embodiment 28. The method of any one of the embodiments 1 to 27, wherein the processing further includes determining the concentration of one or more measurand species.

Embodiment 29. The method of any one of the embodiments 1 to 28, wherein the sample medium is a gas from an artificial or natural process.

Embodiment 30. The method of any one of the embodiments 1 to 29, wherein the light source is a diode laser controlled by a continuous and variable drive current.

Embodiment 31. The method of any one of the embodiments 1 to 30, wherein an optical diffuser is located substantially in front of the photodetector.

Embodiment 32. An absorption spectroscopy system, comprising:
 a light source for emitting a photon beam;
 a controller for controlling the light source to emit a wavelength modulated photon beam, wherein the controller is also adapted to apply at least one tapering burst signal modulation to the photon beam;
 a photodetector for detecting the modulated photon beam after transmission through a sample medium;
 a signal processing unit for processing the detected beam to obtain at least one detected burst signal and to measure absorption effects of one or more measurands, wherein the processing unit is adapted to compare the at least one detected burst signal with the applied at least one burst signal modulation to determine intensity fluctuations of the incident light that are separate from absorption effects of the measurand(s), and to correct for the effects of the determined intensity fluctuations for increased accuracy of measurement of the absorption effects of the measurand(s).

Embodiment 33. The system of embodiment 32, comprising means for selecting at least one wavelength zone location and/or duration for the at least one burst signal, to isolate the burst signal from a measured absorption line of the measurand(s).

Embodiment 34. The system of embodiment 32 or 33, wherein the at least one tapered burst signal modulation has a shape that is different from any naturally occurring absorption shape or optical interference fringe effect.

Embodiment 35. The system of any one of embodiments 32 to 34, wherein at least one of the amplitude and the width of the tapered burst signal modulation is chosen to be substantially larger than any expected natural background fluctuation.

Embodiment 36. The system of any one of embodiments 32 to 35, wherein the controller is adapted to apply multiple tapering burst signal modulations to the photon beam.

Embodiment 37. The system of any one of embodiments 32 to 36, wherein the light source is a tunable diode laser, and wherein the controller is configured to repeatedly scan the laser's bias current across a range of values at a scan rate having a period T, for wavelength modulation of the laser's beam of light, and wherein the duration of the tapering burst signal modulation is less than the period T.

Embodiment 38. The system of embodiments 37, wherein the controller is adapted to apply multiple tapering burst signal modulations to the photon beam within a single scan.

Embodiment 39. The system of embodiment 37 or 38, wherein the position of at least one tapering burst signal modulation is varied between scan cycles.

Embodiment 40. The system of any one of embodiments 36 to 37, wherein the corrected light intensity is calculated based on a selected subset of tapered burst signal modulations, the subset including one or more of the tapered burst signal modulations.

Embodiment 41. The system of any one of embodiments 32 to 40, wherein the tapered burst signal modulation is generated using a window function.

Embodiment 42. The system of embodiment 41, wherein the window function is one of a Tukey window function, a Planck-taper window function, a Kaiser-Bessel window function, a Hamming window function, a Hanning window function, a Blackman window function or a triangular window function.

Embodiment 43. The system of any one of embodiments 32 to 42, wherein the tapered burst signal modulation is one of:
amplitude modulation at fixed phase;
phase modulation at fixed amplitude; or
a combination of phase modulation and amplitude modulation, Embodiment 44. The system of any one of embodiments 32 to 43, wherein the controller is adapted to control one of:
an external modulation device;
a second laser light source comprising a laser diode;
a light emitting diode; or
the laser light source bias current;
for applying a tapered burst signal modulation to the photon beam.

Embodiment 45. The system of any one of embodiments 32 to 44, wherein the sample medium is a gas produced in a chamber associated with an artificial or natural process, and wherein the light source is positioned such that it emits the photon beam through at least a portion of said chamber.

Embodiment 46. The system of any one of embodiments 32 to 44, wherein the sample gas flows through an extractive system, and wherein the light source is positioned such that it emits the photon beam through at least a portion of said extractive system.

Embodiment 47. A method of calibrating an absorption spectroscopy system that comprises a light source and a light detector, the method comprising:
applying at least one modulation burst signal to a beam emitted by the light source;
detecting the modulated beam after transmission through a sample gas;
processing the detected beam to obtain at least one detected modulation burst signal, and comparing at least one detected modulation burst signal with the applied modulation burst signal to identify signal processing anomalies; and
modifying the modulation burst signal to reduce the signal processing anomalies, Embodiment 48. The method of embodiment 47, further comprising modifying the location and/or duration of the at least one modulation burst signal.

Embodiment 49. The method of embodiment 47 or 48, wherein the burst signal is phase modulated at fixed amplitude.

Embodiment 50. The method of embodiment 47 or 48, wherein the burst signal is amplitude modulated at fixed phase.

Embodiment 51. The method of embodiment 47 or 48, wherein the burst signal is both phase and amplitude modulated.

Embodiment 52. The method of any one of embodiments 47 to 51, wherein the light source is a diode laser and the step of applying a modulation burst signal includes modulating the bias current of the diode laser to produce the burst signal.

Embodiment 53. The method of any one of embodiments 47 to 52, wherein the light source is a tunable diode laser and the laser's bias current is ramped up or down across a range of values to scan the laser's output beam across a range of wavelengths; and wherein the method further comprises identifying absorption wavelengths of gases in the sample gas and the step of modifying the modulation burst signal comprises modifying the location of the modulation burst signal within the scanned wavelength range to avoid the identified absorption wavelengths.

The invention claimed is:

1. A method of correcting for the effects of intensity fluctuations of incident light within an absorption spectroscopy system, comprising the steps of:
controlling a light source to emit a wavelength modulated beam of light using a controller;
applying, using the controller, at least one modulation burst signal to perform one or more of modulating the wavelength modulated beam or modulating a separate beam synchronised with the wavelength modulated beam, which at least one modulation burst signal is a tapering signal modulation;
detecting, at a detector, the modulated beam(s) of light after transmission through a sample medium; and
processing, using an electronic detection system coupled to the detector, the detected beam(s) to obtain at least one detected burst signal and to measure absorption effects of one or more measurands, wherein the processing includes comparing the at least one detected burst signal with the applied at least one modulation burst signal to determine intensity fluctuations of the incident light that are separate from absorption effects of the measurand(s), and correcting for the effects of the determined intensity fluctuations for increased accuracy of measurement of the absorption effects of the measurand(s).

2. The method of claim 1 comprising selecting at least one of a wavelength zone or a duration for the at least one burst signal to isolate the burst signal from a measured absorption line of the measurand(s).

3. The method of claim 1, wherein the light source is a tunable diode laser having an associated laser bias current, and the laser's bias current is repeatedly scanned across a range of values at a scan rate having a period T, for wavelength modulation of the laser's beam of light, and wherein the duration of the burst signal is less than the period T.

4. The method of claim 3, wherein the position of at least one burst signal is varied between scan cycles.

5. The method of claim 1, wherein the modulated beam is detected by a photodetector and the processing further comprises:
  processing an output signal from the photodetector to obtain a reference signal proportional to the detected burst signal; and
  using the reference signal to produce a corrected signal that is proportional to the concentration of one of the one or more measurands.

6. The method of claim 5, wherein the processing further includes integrating the reference signal over a time period that is an integer multiple of a period of the modulation burst signal.

7. The method of claim 6, wherein a baseline ramp function is subtracted from the reference signal to correct for selective residual absorption of the measurand and any background chemical species.

8. The method of claim 1, wherein the modulation burst signal is one of:
  amplitude modulated at fixed phase;
  phase modulated at fixed amplitude; or
  both phase and amplitude modulated.

9. The method of claim 1, wherein the frequency of the burst signal is chosen to be equal to a harmonic frequency of the light source modulation frequency used for the spectroscopic measurement of the absorption effects of at least one measurand.

10. The method of claim 9, wherein phase modulation is used to invert the burst signal.

11. The method of claim 1, wherein the light source is a diode laser having an associated bias current, and the step of applying a modulation burst signal includes modulating the bias current of the diode laser to produce the burst signal.

12. The method of claim 1, wherein the detecting and processing steps are carried out by a demodulating detector, and the burst signal is applied using one of: an external modulation device synchronised to the demodulating detector, a secondary diode laser synchronised to the demodulating detector, or a light emitting diode synchronised to the demodulating detector.

13. The method of claim 1, wherein at least one absorption line of at least one measurand is corrected for intensity fluctuations.

14. The method of claim 1, wherein the shape of the tapering signal modulation is chosen to be different from any naturally occurring absorption shape or optical interference fringe effect.

15. The method of claim 1, wherein at least one of the amplitude and the width of the burst signal is chosen to be substantially larger than any expected natural background fluctuation.

16. The method of claim 1, wherein multiple burst signals are used in order to determine the light intensity fluctuations and wherein averaging of the measured light intensity is used to minimise a correction error.

17. The method of claim 16, wherein the corrected light intensity is calculated based on a selected subset of burst signals, the subset including one or more of the multiple burst signals.

18. The method of claim 1, wherein the light source is a tunable diode laser having an associated bias current, and the laser's bias current is ramped up and down across a range of values to vary the laser's output beam across a range of wavelengths; and wherein the method further comprises identifying absorption wavelengths of gases in the sample medium and choosing the location of the modulation burst signal within the wavelength range to avoid the identified absorption wavelengths.

19. The method of claim 1, wherein the tapering signal modulation of the burst signal is generated using a window function.

20. The method of claim 19, wherein the window function is one of a Tukey window function, a Planck-taper window function, a Kaiser-Bessel window function, a Hamming window function, a Hanning window function, a Blackman window function or a triangular window function.

21. The method of claim 1, wherein the burst signal is inverted with respect to at least one absorption feature of the one or more measurands.

22. The method of claim 1, wherein the modulated beam is detected by a photodetector and an optical diffuser is located substantially in front of the photodetector.

23. An absorption spectroscopy system, comprising:
  a light source for emitting a photon beam;
  a controller for controlling the light source to emit a wavelength modulated photon beam, wherein the controller is also adapted to apply at least one tapering burst signal modulation to the photon beam;
  a photodetector for detecting the modulated photon beam after transmission through a sample medium; and
  an electronic detection system for processing the detected beam to obtain at least one detected burst signal and to measure absorption effects of one or more measurands, wherein the electronic detection system is adapted to compare the at least one detected burst signal with the applied at least one burst signal modulation to determine intensity fluctuations of the incident light that are separate from absorption effects of the measurand(s), and to correct for the effects of the determined intensity fluctuations for increased accuracy of measurement of the absorption effects of the measurand(s).

24. The system of claim 23, wherein the at least one tapering burst signal modulation has a shape that is different from any naturally occurring absorption shape or optical interference fringe effect.

25. The system of claim 23, wherein at least one of the amplitude and the width of the tapering burst signal modulation is chosen to be substantially larger than any expected natural background fluctuation.

26. The system of claim 23, wherein the light source is a tunable diode laser having an associated bias current, and wherein the controller is configured to repeatedly scan the laser's bias current across a range of values at a scan rate having a period T, for wavelength modulation of the laser's beam of light, and wherein the duration of the tapering burst signal modulation is less than the period T.

27. The system of claim 26, wherein the controller is adapted to apply multiple tapering burst signal modulations to the photon beam within a single scan.

28. The system of claim 26, wherein the position of at least one tapering burst signal modulation is varied between scan cycles.

29. The system of claim 26, wherein the corrected light intensity is calculated based on a selected subset of tapering burst signal modulations, the subset including one or more of the tapering burst signal modulations.

30. The system of claim 23, wherein the tapering burst signal modulation is generated using a window function.

31. The system of claim 30, wherein the window function is one of a Tukey window function, a Planck-taper window function, a Kaiser-Bessel window function, a Hamming window function, a Hanning window function, a Blackman window function or a triangular window function.

32. The system of claim 23, wherein the tapering burst signal modulation is one of:
   amplitude modulation at fixed phase;
   phase modulation at fixed amplitude; or
   a combination of phase modulation and amplitude modulation.

33. The system of claim 23, wherein the controller is adapted to control one of:
   an external modulation device;
      a second light source comprising a laser diode;
      a light emitting diode; or
      the light source bias current;
   for applying a tapering burst signal modulation to the photon beam.

34. The system of claim 23, wherein the sample medium is one of:
   a gas produced in a chamber associated with an artificial or natural process, and wherein the light source is positioned such that it emits the photon beam through at least a portion of said chamber; or
   a sample gas flowing through an extractive system, and wherein the light source is positioned such that it emits the photon beam through at least a portion of said extractive system.

35. A method of calibrating an absorption spectroscopy system that comprises a light source and a light detector, the method comprising:
   applying, using the controller, at least one modulation burst signal to a beam emitted by the light source;
   detecting, at a detector, the modulated beam after transmission through a sample gas;
   processing, using an electronic detection system coupled to the detector, the detected beam to obtain at least one detected modulation burst signal, and comparing at least one detected modulation burst signal with the applied modulation burst signal to identify signal processing anomalies; and
   modifying the modulation burst signal to reduce signal processing anomalies.

36. The method of claim 35, further comprising modifying one or more of a location or a duration of the at least one modulation burst signal.

37. The method of claim 35, wherein the burst signal is one of:
   phase modulated at fixed amplitude;
   amplitude modulated at fixed phase; or
   both phase and amplitude modulated.

38. The method of claim 35, wherein the light source is a diode laser having an associated bias current and the step of applying a modulation burst signal includes modulating the bias current of the diode laser to produce the burst signal.

39. The method of claim 35, wherein the light source is a tunable diode laser having an associated bias current, and the laser's bias current is ramped up or down across a range of values to scan the laser's output beam across a range of wavelengths; and wherein the method further comprises identifying absorption wavelengths of gases in the sample gas and the step of modifying the modulation burst signal comprises modifying the location of the modulation burst signal within the scanned wavelength range to avoid the identified absorption wavelengths.

* * * * *